US008513295B2

(12) United States Patent
Padmanabhan et al.

(10) Patent No.: US 8,513,295 B2
(45) Date of Patent: Aug. 20, 2013

(54) VIRAL AND FUNGAL INHIBITORS

(75) Inventors: Radhakrishnan Padmanabhan, Bethesda, MD (US); William C. Groutas, Wichita, KS (US); Brent E. Korba, Laurel, MD (US)

(73) Assignees: Georgetown University, Washington, DC (US); Wichita State University, Wichita, KS (US)

( * ) Notice: Subject to any disclaimer, the term of this patent is extended or adjusted under 35 U.S.C. 154(b) by 0 days.

(21) Appl. No.: 13/120,610

(22) PCT Filed: Sep. 23, 2009

(86) PCT No.: PCT/US2009/058039
§ 371 (c)(1),
(2), (4) Date: Jul. 20, 2011

(87) PCT Pub. No.: WO2010/039534
PCT Pub. Date: Apr. 8, 2010

(65) Prior Publication Data
US 2011/0301208 A1    Dec. 8, 2011

Related U.S. Application Data

(60) Provisional application No. 61/099,412, filed on Sep. 23, 2008, provisional application No. 61/179,444, filed on May 19, 2009, provisional application No. 61/220,958, filed on Jun. 26, 2009.

(51) Int. Cl.
*A01N 43/50* (2006.01)
*A61K 31/415* (2006.01)
*C07D 209/00* (2006.01)

(52) U.S. Cl.
USPC .......................................................... 514/396

(58) Field of Classification Search
USPC .......................................... 548/452; 514/396
See application file for complete search history.

(56) References Cited

U.S. PATENT DOCUMENTS

| 3,761,489 | A | | 9/1973 | Grivas | |
|---|---|---|---|---|---|
| 5,605,914 | A | * | 2/1997 | Muller | 514/339 |
| 5,698,579 | A | * | 12/1997 | Muller | 514/416 |
| 5,939,437 | A | * | 8/1999 | Kalindjian et al. | 514/330 |
| 6,492,362 | B1 | * | 12/2002 | Graupe et al. | 514/237.5 |

FOREIGN PATENT DOCUMENTS

| WO | WO 01/42216 | 6/2001 |
|---|---|---|
| WO | 02/081463 A1 | 10/2002 |
| WO | 2004/058704 A2 | 7/2004 |
| WO | 2005/030727 A1 | 4/2005 |
| WO | 2005/037845 A1 | 4/2005 |
| WO | WO 2006/091858 | 8/2006 |

OTHER PUBLICATIONS

Wolfe.*
Vippagunta et al.*
Banker.*
Mahmoud, A.M. et al., Synthesis and biological activities of some new 2-(N-heterocyclic carboxamidomethyl thio) benzoxazoles, benzthiazoles and benzimidazoles. Part VIII. Eur. J. Med. Chem.—Chimica Therapeutica, Jul.-Aug. 1981, 16(4), pp. 383-384.
Ocain S. D. et al; "New Modified Heterocyclic Phenylalanine Derivatives"; Journal of Medicinal Chemistry, American Chemical Society , US, vol. 35, No. 5; Mar. 6, 1992; pp. 823-832.
Mor, Marco et al.; "Biological Studies on 1,2-Benzisothiazole Derivatives" ,Farmaco, Societa Chimica Italiana, Pavia. IT.vol. 51, No. 7; Jan. 1, 1996; pp. 493-501, XP009158306; p. 494; table I; compounds 1-3, 5-7, 14-19. 24-26.
Thomas J Schwan et al; Synthesis of Antifungal 2-Substituted Phthalimidines .J of Pharmaceutical Science vol. 67, No. 6; Jun. 1, 1978; pp. 863-864; XP001465016, p. 864, col. 1; compounds V.,VI.
Breytenbach. J.C. et al; "Synthesis and Antimicrobial Activity of Some Isoindolin-1-ones Derivatives", Bioorganic and Medicinal Chemistry Letters.; Mar. 13, 2000; School of Pharmacy; Republic of South Africa; vol. 10, pp. 1629-1631, XP002673634, p. 1631, col. 1.
Database Registry [Online] 1 Chemical Abstracts Service, Columbus, Ohio, US; Jul. 1, 2008; "2H-Isoindole-2-propanamide, N-(2,3-dihydro-1,4-benzodioxin-6-y1)-1,3-d ihydro-l-oxo.beta.-2-thienyl-", XP002673865, Database accession No. 1031992-76-3.
Database Registry [Online] 1Chemical Abstracts Service, Columbus,Ohio, US; Jul. 1, 2008; "2H-isoindole-2-propanamide, N-(l,3-benzodioxol-5-ylmethyl)-1,3-dihydro -1-oxo.beta.-2-thienyl-",XP002673866, Database accession No. 1031992-70-7.
Database Registry [Online]; Chemical Abstracts Service, Columbus,Ohio, US; Jul. 1, 2008; Benzoic acid, 3-[[1,3-dihydro-1-oxo-2H-isoindo1-2-yl)-1-oxo-3-(2 thienyl) propyl]amino]-, ethylester ,XP002673867, Database accession No. 1031992-68-3.
Database Registry [Online]; Chemical Abstracts Service, Columbus, Ohio Jul. 1, 2008 (2008-07-01); "2H-Isoindole-2-propanamide, 1,3-dihydro-l-oxo-N-(phenylmethyl)-.beta.- 2-thienyl-", XP002673868, Database accession No. 1031992-66-1.
Database Registry [Online]; Chemical Abstracts Service, Columbus. Ohio, US; Jul. 1, 2008; "2H-Insoindole-2-acetamide, N-(2,6-dimethylpheny1)-1,3-dihydro-l-oxo-alpha.-(phenylmethyl)-". XP002673869, Database accession No. 1031934-82-3.
Database Registry [Online]; Chemical Abstracts Service, Columbus,Ohio, US; Jun. 24, 2008; 2H-Insoindole-2-propanamide, 1,3-dihydro-N-(2-methylpheny1)-1-oxo-.beta.-2-thienyl-II, XP002673870, Database accession No. 1030124-62-9.
Database Registry [Online]; Chemical Abstracts Service. Columbus, Ohio. US; Jun. 24, 2008;"2H-Insoindole-2-propanamide,1,3. dihydro-N-(2methylpheny1)-1-oxo-.beta.-2-thienyl-"; XP002673871, Database accession No. 1030124-62-9.
Database Registry [Online]; Chemical Abstracts Service, Columbus, Ohio,US; Jun. 24, 2008; "2H-insoindole-2-propanamide, N-[(4-fluorophenyl)methy1]-1.3-dihydro-l-oxo-.beta..-2-thienyl-"; XP002673872, Database accession No. 1030124-51-6.
Database Registry [Online]; Chemical Abstracts Service,Columbus, Ohio, US; Jun. 24, 2008, "2H-Isoindole-2 propanamide.1,3-dihydro-l-oxo-N-(2-phenylethyl)-.beta.-2-thienyl",; XP002673873, I accession No. 1030124-46-9.

(Continued)

Primary Examiner — Paul V. Ward
(74) Attorney, Agent, or Firm — Frommer Lawrence & Haug LLP; Blaine M. Hackman

(57) ABSTRACT

Novel classes of viral and fungal inhibitors are disclosed. These compounds are useful in treating, preventing, and/or ameliorating viral infections such as, for example, Hepatitis C Virus, West Nile Virus, Dengue Virus, and Japanese Encephalitis Virus, and fungal infections such as, for example, candidiasis.

9 Claims, 8 Drawing Sheets

(56) References Cited

OTHER PUBLICATIONS

Database Registry [Online]; Chemical Abstracts Service, Columbus, Ohio, US; Jun. 24, 2008; Benzoic acid.44[[3-(1.3-dihydro-l-oxo-2H-isoindol-2-y0-1-oxo-3-(2-thienyl)propyllamino.

Database Registry [Online];Chemical Abstracts Service, Columbus. Ohio, US; Jun. 24, 2008; "2H-Insoindole-2-propanamide.1.3-dihydro-N-(4-methoxyphenyl)-1-oxo,beta.-2-thienyl"; XP002673875, Database accession No. 1030124-26-5.

Database Registry [Online]; Chemical Abstracts Service. Columbus,Ohio, US; Jun. 22, 2008; "Benzoic acid.4-[[3-(1.3-dihydro-l-oxo-2H-isoindol-2-y1)-1-oxo-3-(2-thienyl)propyl-lamino-. methyl ester"; XP002673876, 1029764-48-4.

* cited by examiner

VIRAL AND FUNGAL INHIBITORS

STATEMENT REGARDING FEDERALLY SPONSORED RESEARCH OR DEVELOPMENT

This invention was made with government support under grants R01 AI070791, R32 AI577045, and U54 AI057168 awarded by the National Institutes of Health. The government has certain rights in the invention.

BACKGROUND

Viral infections such as hepatitis C virus (HCV) and *Flavivirus* are major causes of morbidity and mortality around the world. Chronic infection with HCV, for example, is a major health problem that affects more than 170 million people worldwide and is a causative agent of liver cirrhosis, hepatocellular carcinoma, and liver failure. While treatments exist for HCV, these treatments often have limited efficacy, serious side effects, high expense, and can result in drug resistance. Further, *Flaviviruses* such as West Nile virus (WNV), Japanese Encephalitis virus, and Dengue virus (e.g., the four known serotypes of Dengue virus (DEN-1-4)) are significant human pathogens that cause millions of infections each year and result in considerable morbidity and mortality. DEN viruses cause a simple and self-limiting disease in humans called dengue fever (DF), which often resolves in a week to 10 days. However, more severe forms of the disease, known as Dengue hemorrhagic fever (DHF) and Dengue shock syndrome (DSS) common in areas endemic to DEN 1-4 lead to considerable morbidity and mortality. According to World Health Organization estimates, 50-100 million cases of DEN infections in tropical and subtropical countries occur each year. WNV was introduced into the western hemisphere during an outbreak in the United States in 1999. In the following years, WNV has spread throughout much of North America and has become a public health concern. Most WNV infections are asymptomatic; however, about 20% of cases are associated with mild flu-like symptoms. A small fraction of these cases progress to more severe clinical manifestations including encephalitis and/or flaccid paralysis. There are no approved vaccines or antiviral therapeutics available for either DEN- or WNV-infected human.

Additionally, fungal infections are also significant causes of death in human and animal populations. Candidiasis is an infection that is caused by fungi and yeasts, and can be life threatening for those with weakened immune systems. While there are treatments for candidiasis, these treatments often result in drug resistance.

SUMMARY

Novel classes of viral and/or fungal inhibitors useful in treating, preventing, and/or ameliorating viral infections (e.g., Hepatitis C Virus and *Flavivirus* infections) and fungal infections (e.g., candidiasis) are disclosed along with methods of making and using them. A first class of viral and/or fungal inhibitors comprises compounds of the following formula:

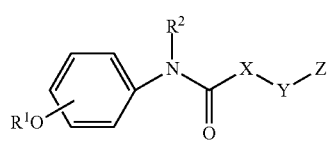

and includes pharmaceutically acceptable salts and prodrugs thereof. In this class of molecules, $R^1$ and $R^2$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; X is $CR^3R^4$, $NR^5$, O, and S, wherein $R^3$, $R^4$, and $R^5$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; Y is S or $(CH_2)_n$, wherein n is 0 to 5; and Z is substituted or unsubstituted aryl, substituted or unsubstituted heteroaryl, or $(C=O)AR^6$, wherein A is O, S, NH, or N(H)O, and $R^6$ is selected from substituted or unsubstituted aryl, substituted or unsubstituted heteroaryl, substituted or unsubstituted arylalkyl, and substituted or unsubstituted heteroarylalkyl.

A second class of viral and/or fungal inhibitors comprises compounds of the following formula:

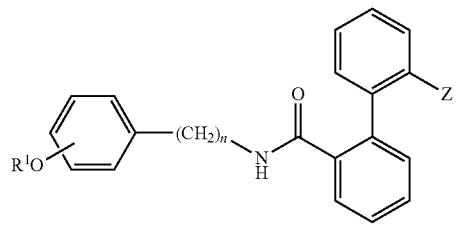

or pharmaceutically acceptable salts or prodrugs thereof. In this class of molecules, n is 0 to 5; $R^1$ and $R^2$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and Z is substituted or unsubstituted aryl, substituted or unsubstituted heteroaryl, or $(C=O)AR^6$, where A is O, S, NH, or N(H)O, and $R^6$ is selected from substituted or unsubstituted aryl, substituted or unsubstituted heteroaryl, substituted or unsubstituted arylalkyl, and substituted or unsubstituted heteroarylalkyl.

A third class of viral and/or fungal inhibitors comprises compounds of the following formula:

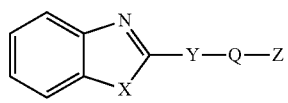

or pharmaceutically acceptable salts or prodrugs thereof. In this class of compounds, Q is —C(O)CH$_2$— or —CH$_2$C(O)—; X is O, S, or NH; Y is S or NH; and Z is substituted or unsubstituted thio, substituted or unsubstituted amino, substituted or unsubstituted aryl, or substituted or unsubstituted heteroaryl.

A fourth class of viral and/or fungal inhibitors comprises compounds of the following formula:

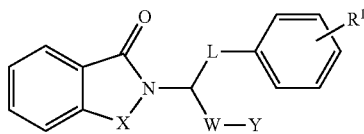

or pharmaceutically acceptable salts or prodrugs thereof. In this class of compounds, L is substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{1-8}$ heteroalkyl, substituted or unsubstituted C$_{2-8}$ heteroalkenyl, or substituted or unsubstituted C$_{2-8}$ heteroalkynyl; R$^1$ is hydrogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl; W is —C(O)NR$^2$—, —C(O)NR$^3$—NR$^4$C(O)—, or substituted or unsubstituted heteroaryl, wherein R$^2$, R$^3$, and R$^4$ are each independently selected from hydrogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl; X is CH$_2$ or S; and Y is hydrogen, hydroxy, alkoxy, substituted or unsubstituted amino, substituted or unsubstituted thio, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A fifth class of viral and/or fungal inhibitors comprises compounds of the following formula:

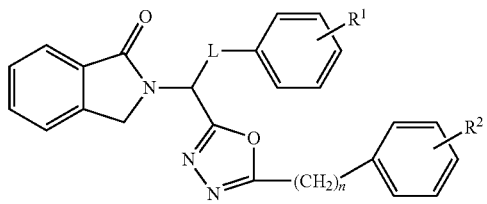

or pharmaceutically acceptable salts or prodrugs thereof. In this class of compounds, n is 0 to 5; L is substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{1-8}$ heteroalkyl, substituted or unsubstituted C$_{2-8}$ heteroalkenyl, or substituted or unsubstituted C$_{2-8}$ heteroalkynyl; and R$^1$ and R$^2$ are each independently selected from hydrogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A sixth class of viral and/or fungal inhibitors comprises compounds of the following formula:

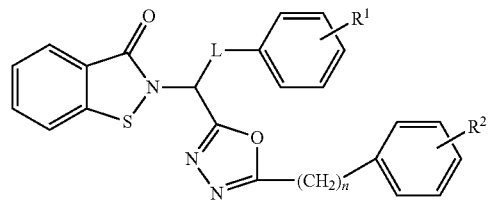

or pharmaceutically acceptable salts or prodrugs thereof. In this class of compounds, n is 0 to 5; L is substituted or unsubstituted C$_{1-8}$ alkyl, substituted or unsubstituted C$_{2-8}$ alkenyl, substituted or unsubstituted C$_{2-8}$ alkynyl, substituted or unsubstituted heteroalkyl, substituted or unsubstituted heteroalkenyl, or substituted or unsubstituted heteroalkynyl; and R$^1$ and R$^2$ are each independently selected from hydrogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

A seventh class of viral and/or fungal inhibitors comprises compounds of the following formula:

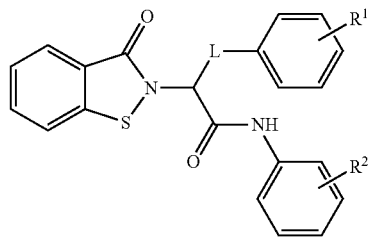

or pharmaceutically acceptable salts or prodrugs thereof. In this class of compounds, L is substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{1-8}$ heteroalkyl, substituted or unsubstituted C$_{2-8}$ heteroalkenyl, or substituted or unsubstituted C$_{2-8}$ heteroalkynyl; and R$^1$ and R$^2$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

An eighth class of viral and/or fungal inhibitors comprises compounds of the following formula:

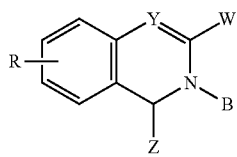

or pharmaceutically acceptable salts or prodrugs thereof. In this class of molecules, B is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl; R is hydrogen, halogen, hydroxy, alkoxy, nitro, substituted or unsubstituted sulfonyl, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl; W is substituted or unsubstituted carbonyl, substituted or unsubstituted imino, substituted or unsubstituted thiocarbonyl, or substituted or unsubstituted thio; Y is N or $CR^1$, wherein $R^1$ is hydrogen, halogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl; and Z is =O, =S, =$NR^2$, or —$NR^3R^4$, wherein $R^2$, $R^3$, and $R^4$ are each independently selected from hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl, wherein if B is —$CH_2$—$CH_3$, W is not

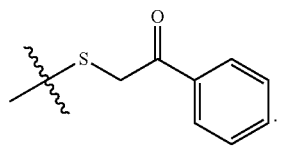

A ninth class of viral and/or fungal inhibitors comprises compounds of the following formula:

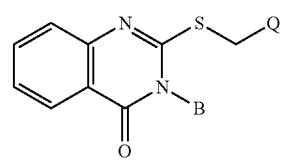

or pharmaceutically acceptable salts or prodrugs thereof. In this class of molecules, B is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl; and Q is —$C(O)R^1$, —$C(O)OR^2$, —$C(O)NHR^2$, —$C(O)NHSO_2R^1$, —$C(O)NHNHR^3$,

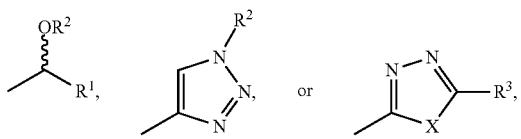

wherein $R^1$ is substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; $R^2$ is hydrogen or $R^1$; $R^3$ is $R^2$, —$C(O)R^1$, or —$C(O)OR^2$; and X is O or S, wherein if B is —$CH_2$—$CH_3$, Q is not

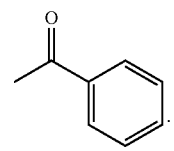

A tenth class of viral and/or fungal inhibitors comprises compounds of the following formula:

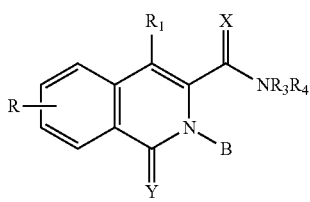

or pharmaceutically acceptable salts or prodrugs thereof. In this class of molecules, B is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl; R is hydrogen, halogen, hydroxy, alkoxy, nitro, substituted or unsubstituted sulfonyl, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl; $R^1$ is hydrogen, halogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl; $R^3$ and $R^4$ are each independently selected from hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl; and X and Y are each independently selected from 0, S, and $NR^2$, wherein $R^2$ is hydrogen, hydroxy, alkoxy, substituted or unsubstituted amino, substituted or unsubstituted thio, substituted or unsubstituted $C_{i-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl.

Also provided herein are novel compositions including the compounds described herein and pharmaceutically acceptable carriers.

Methods for the treatment of viral infections, such as Hepatitis C and *Flavivirus* infections (e.g., West Nile Virus, Dengue Virus, and Japanese Encephalitis Virus), in a subject include administering to the subject a therapeutically effective amount of the compounds and/or compositions described herein. A method for the prevention of viral infections is also provided, which includes administering to the subject a therapeutically effective amount of the compounds and/or compositions described herein. The methods of treating or preventing viral infections can further include administering a second compound or composition, wherein the second compound or composition includes an antiviral compound (e.g., a nucleoside polymerase inhibitor, a non-nucleoside polymerase inhibitor, or a protease inhibitor).

Methods of treating and preventing fungal infections, such as candidiasis and fluconazole resistant fungal infections, in a subject are also provided. The methods include administering to the subject a therapeutically effective amount of the compounds and/or compositions described herein. In some examples, the subject is immunocompromised. The methods of treating or preventing fungal infections can further include administering to the subject a second compound or composition, wherein the second compound or composition includes an antifungal, an antiviral, or mixtures thereof (e.g., a triazole, a thiazole, an imidazole, a polyene, an enchinocandin, an allylamine, a nucleoside polymerase inhibitor, a non-nucleoside polymerase inhibitor, a protease inhibitor, a nucleoside or nucleotide reverse transcriptase inhibitor, a non-nucleoside reverse transcriptase inhibitor, an entry inhibitor, an assembly inhibitor, and mixtures thereof).

DETAILED DESCRIPTION

Figure 1:
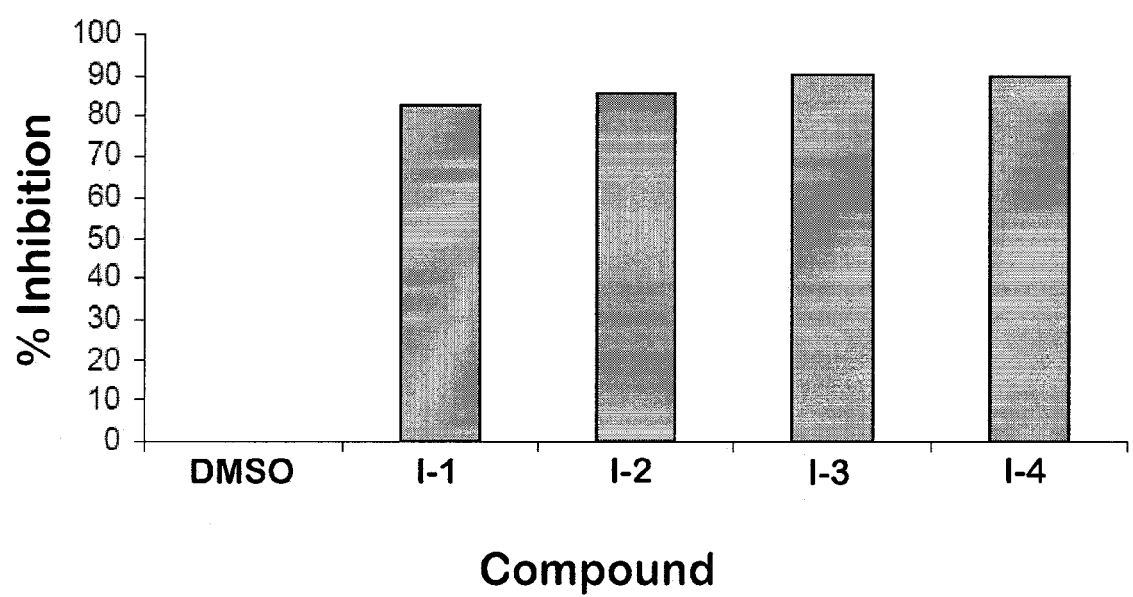
FIG. 1 is a chart showing the percent inhibition of West Nile Virus protease by compounds I-1, I-2, I-3, and I-4 compared to DMSO (0.1%) control.
Figure 2:
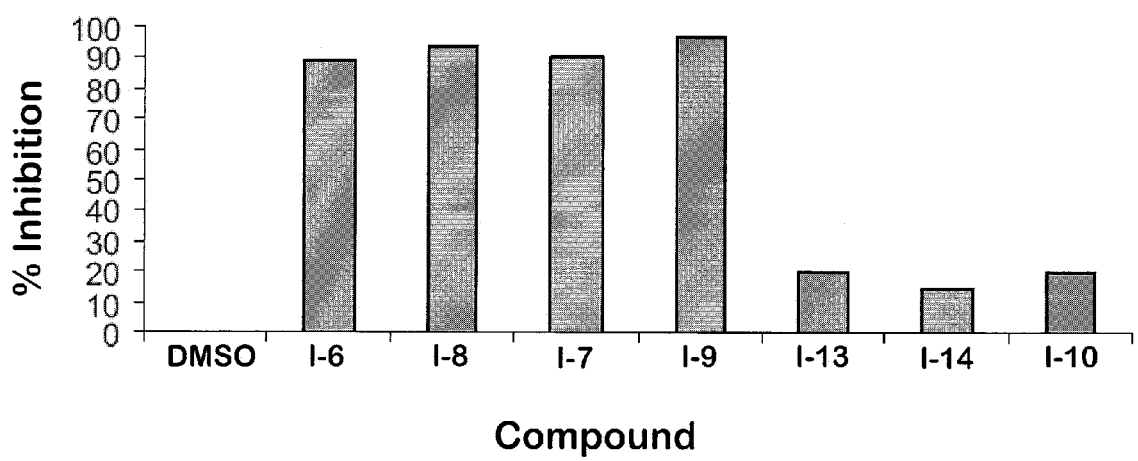
FIG. 2 is a chart showing percent inhibition of West Nile Virus protease by compounds I-6, I-7, I-8, I-9, I-10, I-13, and I-14 compared to DMSO (0.1%) control.
Figure 3:
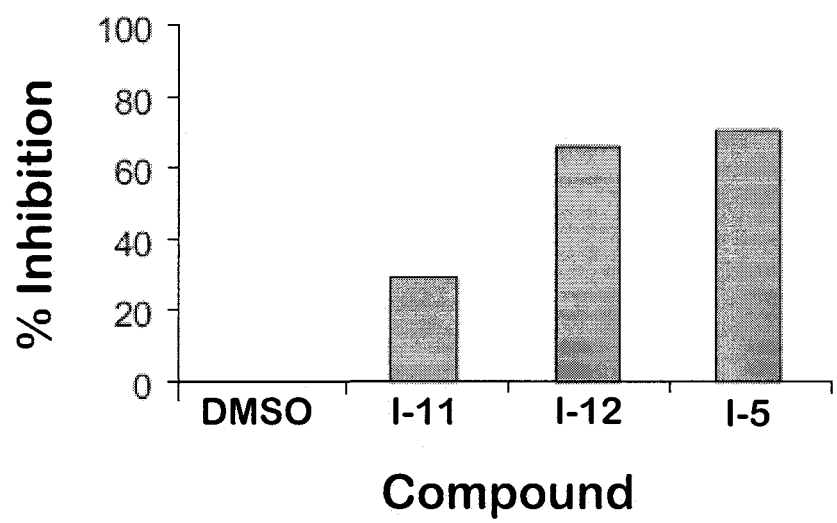
FIG. 3 is a chart showing percent inhibition of West Nile Virus protease by compounds 1-5, I-11, and 1-12 compared to DMSO (0.1%) control.
Figure 4:
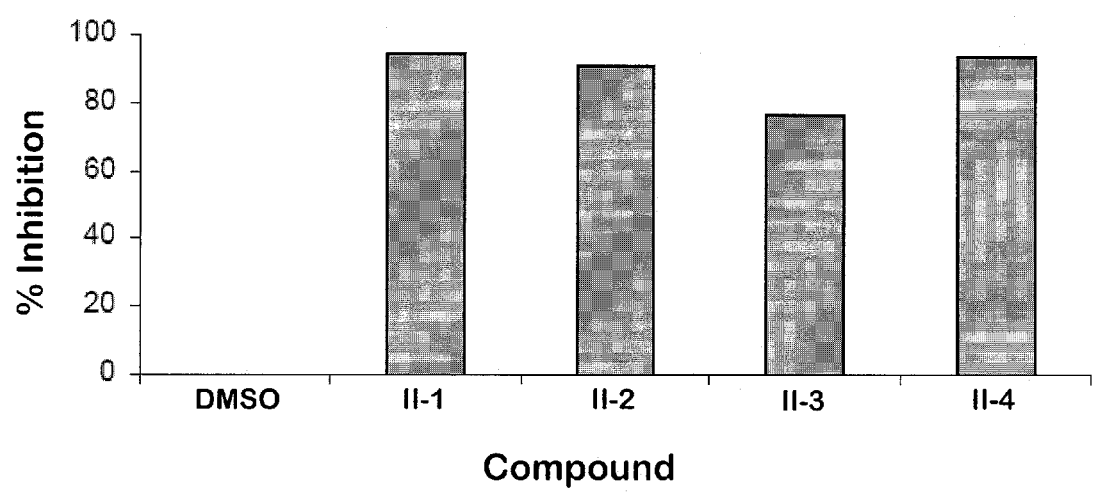
FIG. 4 is a chart showing percent inhibition of West Nile Virus protease by compounds II-1, II-2, II-3, and II-4 compared to DMSO (0.1%) control.
Figure 5:
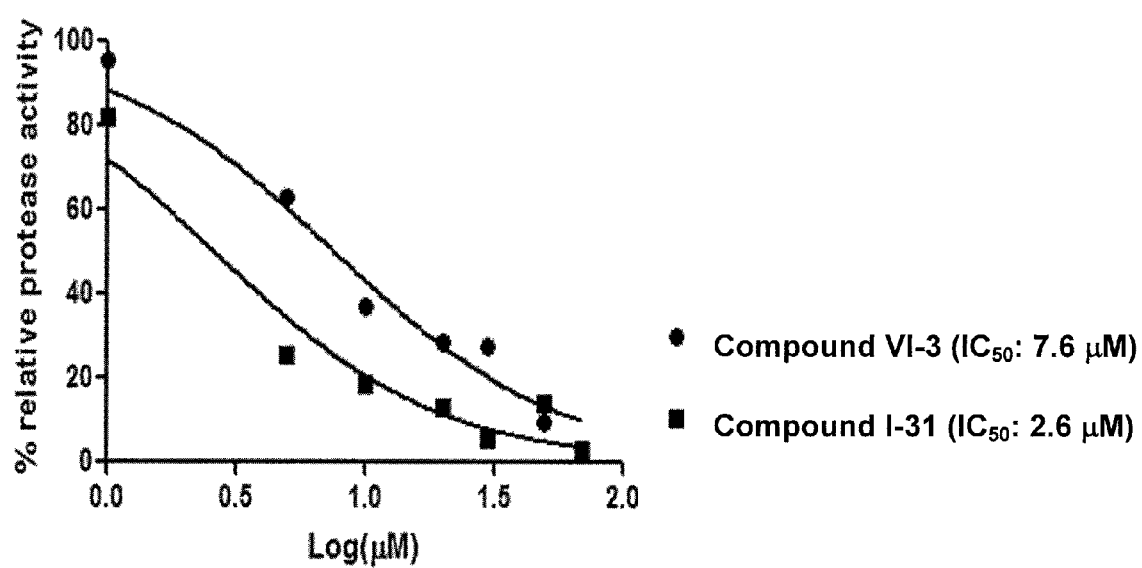
FIG. 5 is a graph showing inhibition of West Nile Virus protease by compounds I-31 and VI-3.
Figure 6:
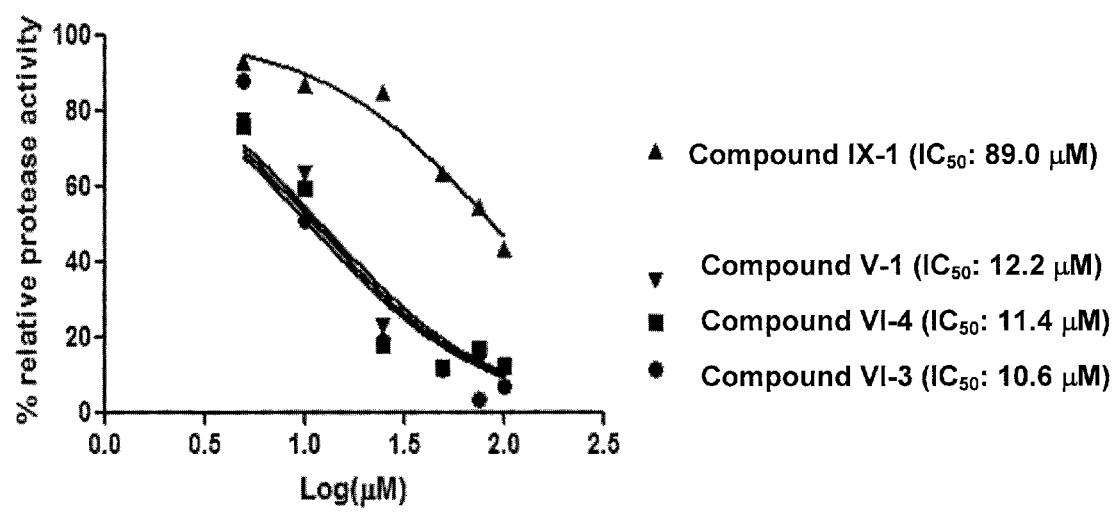
FIG. 6 is a graph showing inhibition of Dengue protease by compounds V-1, VI-4, VI-3, and IX-1.
Figure 7:
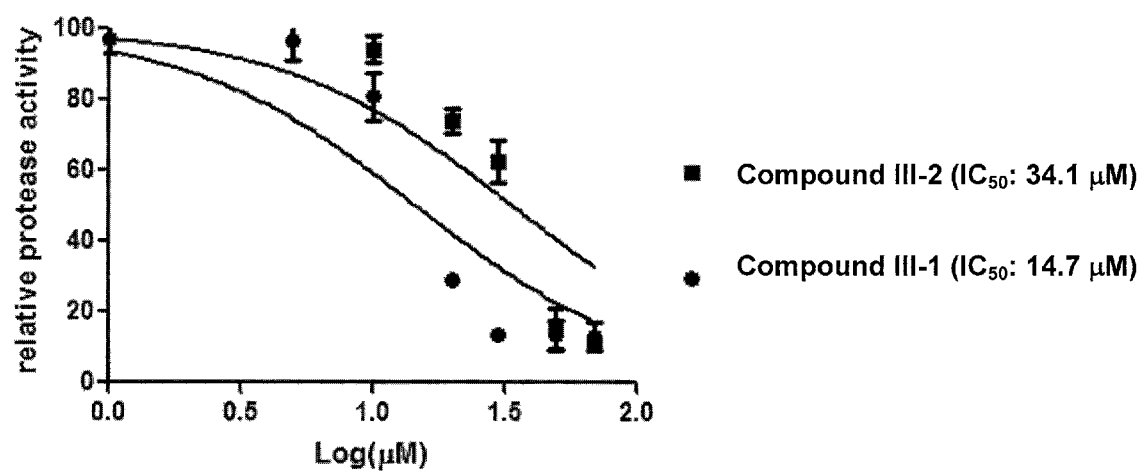
FIG. 7 is a graph showing inhibition of West Nile Virus protease by compounds III-1 and III-2.

Novel classes of viral and/or fungal inhibitors (e.g., *Flavivirus* serine protease inhibitors, HCV inhibitors, and candidiasis inhibitors) are disclosed. These compounds are useful in treating, preventing, and/or ameliorating viral infections (e.g., Hepatitis C and *Flavivirus* infections such as, for example, West Nile Virus, Dengue Virus, and Japanese Encephalitis Virus) and/or fungal infections (e.g., candidiasis), along with methods of making and using them.

A first class of viral and/or fungal inhibitors comprises compounds represented by Compound I:

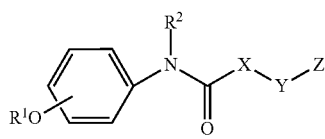

or pharmaceutically acceptable salts or prodrugs thereof.

In Compound I, $R^1$ and $R^2$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, e.g., phenyl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In one example, $R^1$ is a phenyl group and $R^2$ is a hydrogen.

Also, in Compound I, X is $CR^3R^4$, $NR^5$, O, or S, where $R^3$, $R^4$, and $R^5$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl.

Additionally, in Compound I, Y is S or $(CH_2)_n$, where n is 0 to 5.

Further, in Compound I, Z is substituted or unsubstituted aryl, substituted or unsubstituted heteroaryl, or $(C=O)AR^6$, wherein A is O, S, NH, or N(H)O, and $R^6$ is selected from substituted or unsubstituted aryl, substituted or unsubstituted heteroaryl, substituted or unsubstituted arylalkyl, and substituted or unsubstituted heteroarylalkyl.

As used herein, the terms alkyl, alkenyl, and alkynyl include straight- and branched-chain monovalent substituents. Examples include methyl, ethyl, isobutyl, 3-butynyl, and the like. Heteroalkyl, heteroalkenyl, and heteroalkynyl are similarly defined but may contain O, S, or N heteroatoms or combinations thereof within the backbone. The term cycloalkyl as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term heterocycloalkyl is a type of cycloalkyl group as defined above, and is included within the meaning of the term cycloalkyl, where at least one of the carbon atoms of the ring is replaced with a heteroatom such as, but not limited to, nitrogen, oxygen, sulfur, or phosphorus.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include, furan, pyrrole, thiophene, imidazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, cycloalkyl, aryl, heteroalkyl, heteroalkenyl, heteroalkynyl, heterocycloalkyl, and heteroaryl molecules used herein can be substituted or unsubstituted. As used herein, the term substituted includes the addition of an alkyl, alkenyl, alkynyl, cycloalkyl, aryl, heteroalkyl, heteroalkenyl, heteroalkynyl, heterocycloalkyl, or heteroaryl group (as described herein) to a position attached to the main chain of the alkyl, alkenyl, alkynyl, cycloalkyl, aryl, heteroalkyl, heteroalkenyl, heteroalkynyl, heterocycloalkyl, or heteroaryl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, cycloalkyl, aryl, heteroalkyl, heteroalkenyl, heteroalkynyl, heterocycloalkyl, or heteroaryl has a full complement of hydrogens, i.e., commensurate with its saturation level, with no substitutions, e.g., linear decane ($—(CH_2)_9—CH_3$).

The $R^1O—$ group of Compound I is located at the ortho, meta, or para position of its phenyl ring.

The —X—Y—Z group of Compound I can have, for example, the following Structure A1:

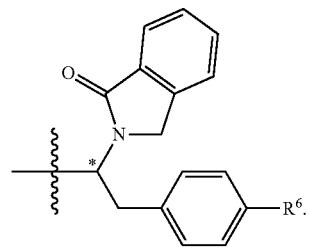

In Structure A1, the asterisk, i.e., *, indicates a chiral center about which Structure A can adopt either a D-enantiomer configuration or an L-enantiomer configuration. In Structure A1, $R^6$ is, for example, either H or OH.

Additionally, the —X—Y—Z group of Compound I can have, for example, the following Structure A2:

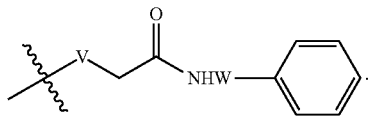

In Structure A2, V is $CR^7R^8$ or $NR^9$ and $R^7$, $R^8$, and $R^9$ are each independently selected from hydrogen, substituted or unsubstituted $C_{1-12}$ alkyl, substituted or unsubstituted $C_{1-12}$haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. Further in Structure A2, W is $(CH_2)—$ or $O(CH_2)—$ and n is 0, 1, or 2.

Further, the —X—Y—Z group of Compound I can have, for example, the following Structure A3:

A3

In Structure A3, Q is —O— or —NH—O—; m is 1, 2, or 3; and n is 0, 1, or 2.

Also, the —X—Y—Z group of Compound I can have, for example, the following Structure A4:

A4

In Structure A4, L is substituted or unsubstituted alkyl or substituted or unsubstituted heteroalkyl. In some examples, L is $(CH_2)_n$, and n is 0, 1, 2, or 3. Further in Structure A4, $R^{10}$ is hydrogen, halogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

Additionally, the —X—Y—Z group of Compound I can have, for example, the following Structure A5:

A5

Also, the —X—Y—Z group of Compound I can have, for example, the following Structure A6:

A6

Additionally, the —X—Y—Z group of Compound I can have, for example, the following Structure A7:

A7

Further examples of Compound I are as follows:

I-1

I-2

I-3

I-4

I-5

I-6

I-7
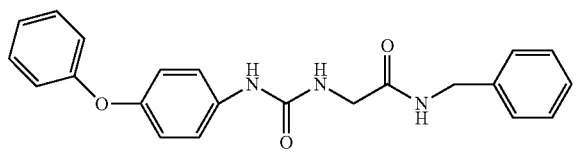
I-8
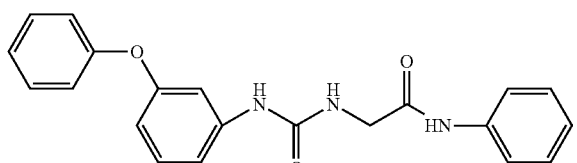
I-9
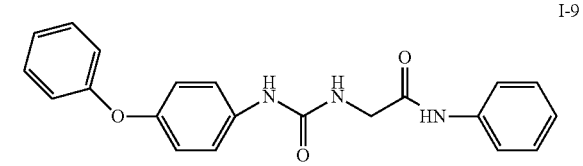
I-10
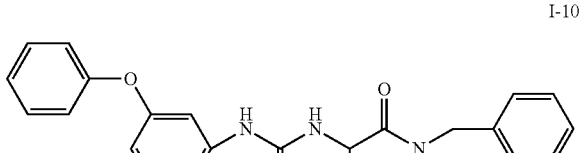
I-11
I-12
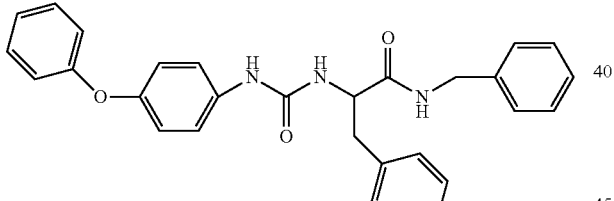
I-13
I-14
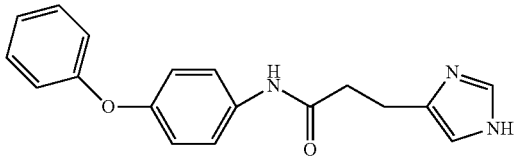
I-15
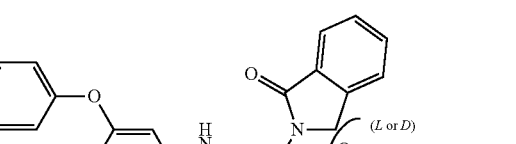
I-16
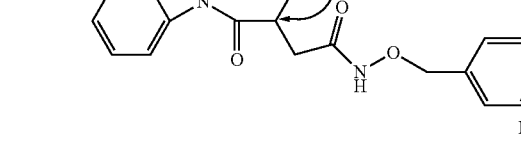
I-17
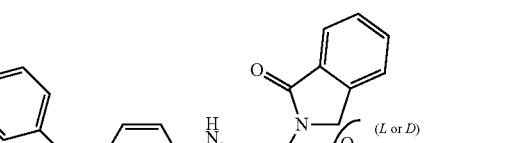
I-18
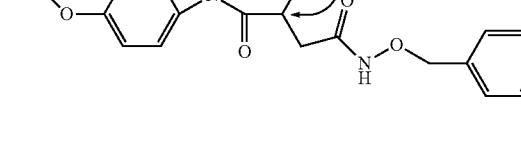
I-19

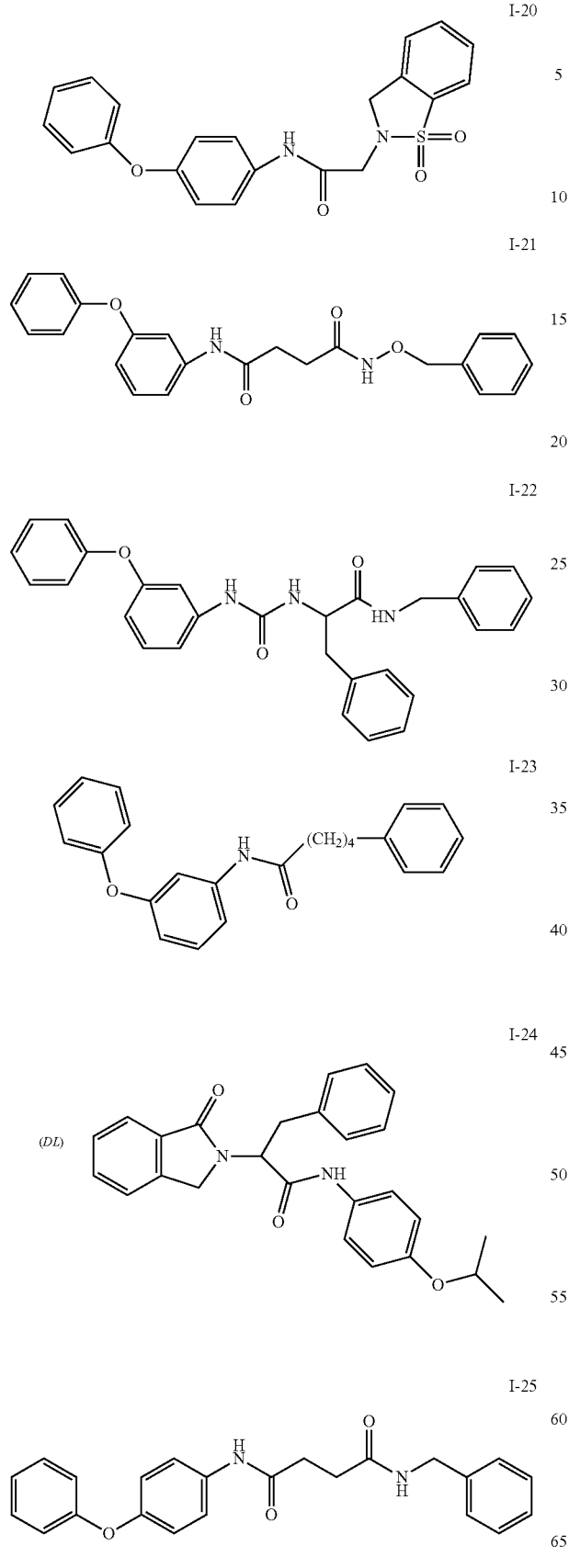
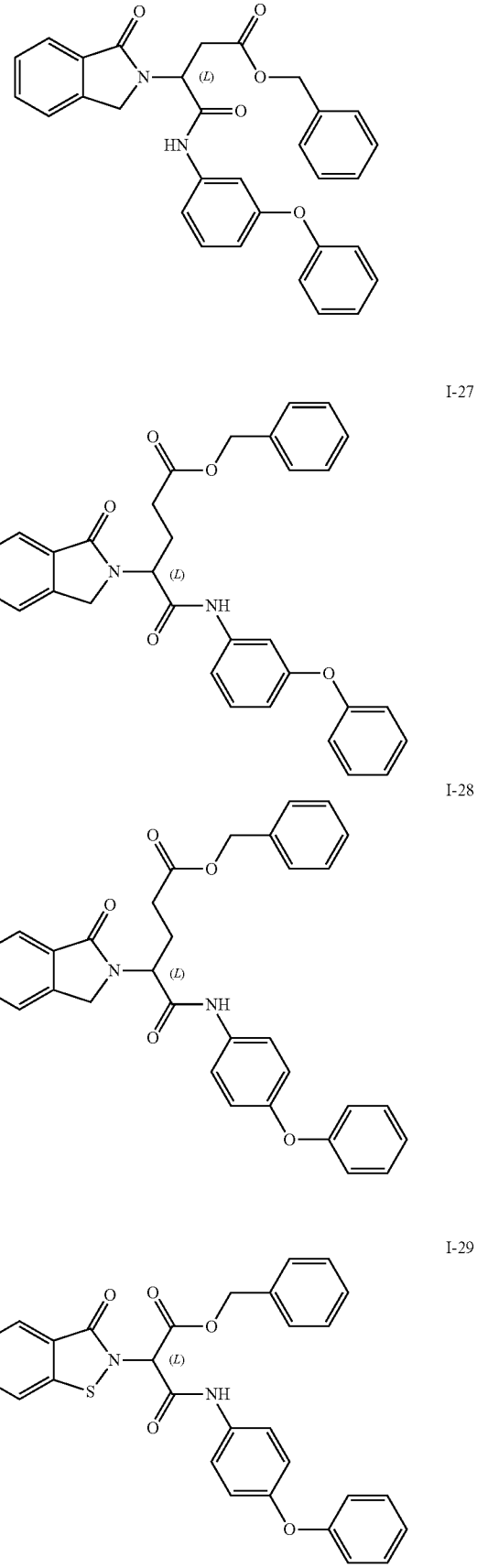

I-30
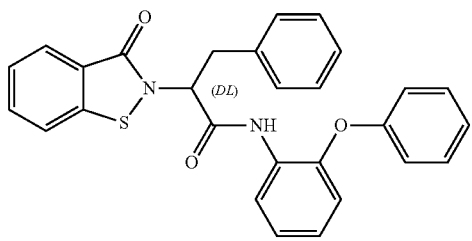

I-31
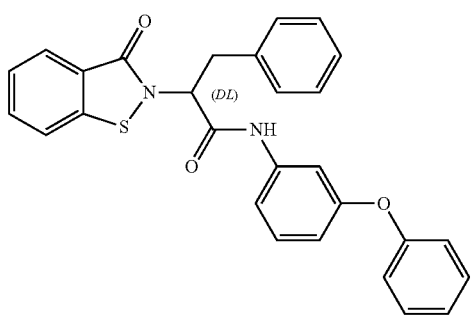

I-32
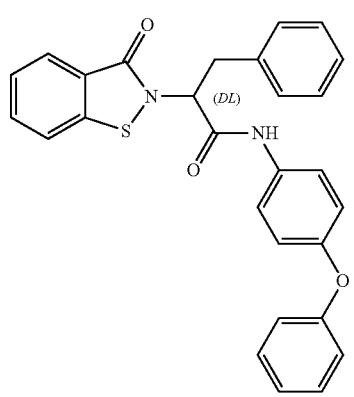

I-33
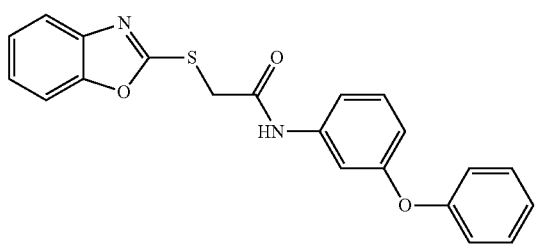

A second class of viral and/or fungal inhibitors comprises compounds represented by Compound II:

II
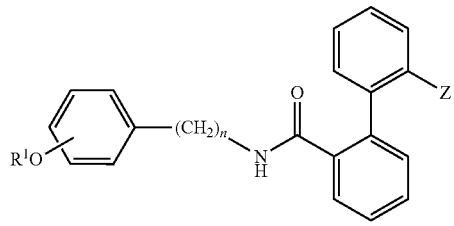

or pharmaceutically acceptable salts or prodrugs thereof.

In Compound II, n is 0 to 5.

Also in Compound II, $R^1$ and $R^2$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, e.g., phenyl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In one example, $R^1$ is a phenyl group and $R^2$ is a hydrogen.

Further in Compound II, Z is substituted or unsubstituted aryl, substituted or unsubstituted heteroaryl, or $(C=O)AR^6$, where A is O, S, NH, or N(H)O, and $R^6$ is selected from substituted or unsubstituted aryl, substituted or unsubstituted heteroaryl, substituted or unsubstituted arylalkyl, and substituted or unsubstituted heteroarylalkyl.

The $R^1O$— group of Compound II is located at either the meta or para position of its phenyl ring.

The —Z group of Compound II can have, for example, the following Structure B1:

B1
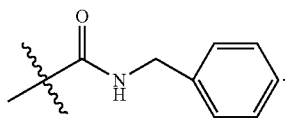

Additionally, the —Z group of Compound II can have, for example, the following Structure B2:

B2
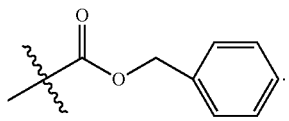

Further examples of Compound II are as follows:

II-1
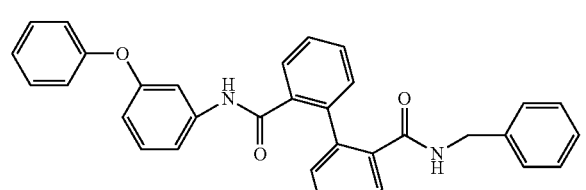

II-2
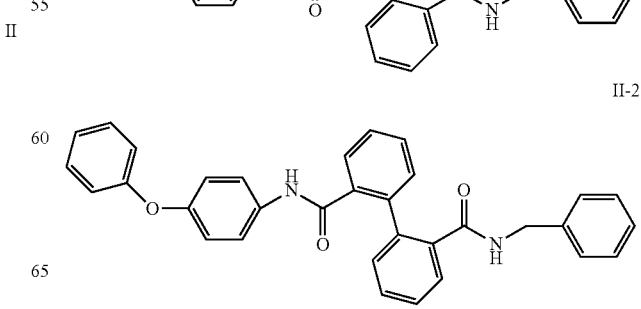

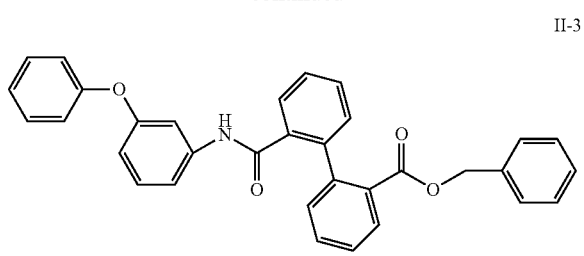

II-3

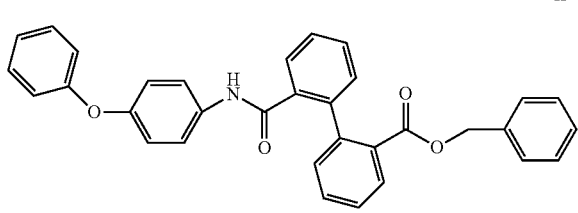

II-4

A third class of viral and/or fungal inhibitors comprises compounds represented by Compound III:

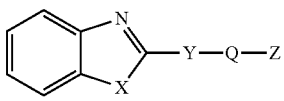

III or pharmaceutically acceptable salts or prodrugs thereof.

In Compound III, Q is —C(O)CH$_2$— or —CH$_2$C(O)—.

Also in Compound III, X is O, S, or NH.

Additionally in Compound III, Y is S or NH.

Further in Compound III, Z is substituted or unsubstituted thio, substituted or unsubstituted amino, substituted or unsubstituted aryl, or substituted or unsubstituted heteroaryl.

The —Z group of Compound III can have, for example, the following Structure C1:

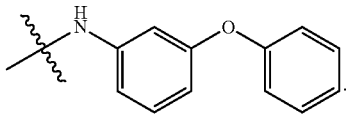

C1

Additionally, the —Z group of Compound III can have, for example, the following Structure C2:

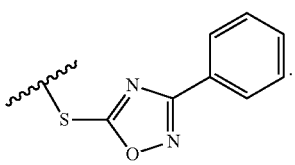

C2

In some examples of Compound III, if Q is —C(O)CH$_2$—, X is S, and Y is NH, Z is not the following Structure C3:

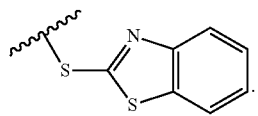

C3

Further examples of Compound III include Compound I-33 and the following compound:

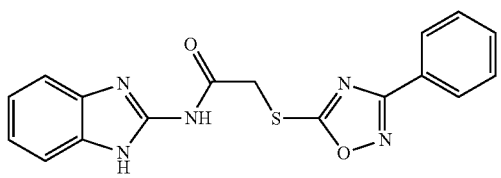

III-1

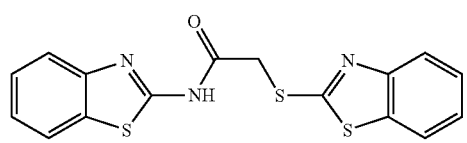

III-2

A fourth class of viral and/or fungal inhibitors comprises compounds represented by Compound IV:

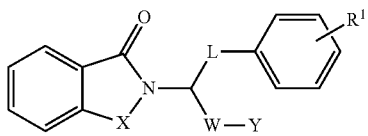

IV or pharmaceutically acceptable salts or prodrugs thereof.

In Compound IV, L is substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{1-8}$heteroalkyl, substituted or unsubstituted C$_{2-8}$ heteroalkenyl, or substituted or unsubstituted C$_{2-8}$ heteroalkynyl.

Also in Compound IV, R$^1$ is hydrogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

Additionally in Compound IV, W is —C(O)NR$^2$—, —C(O)NR$^3$—NR$^4$C(O)—, or substituted or unsubstituted heteroaryl, wherein R$^2$, R$^3$, and R$^4$ are each independently selected from hydrogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, W is —C(O)NH—.

The —W group of Compound IV can have, for example, the following Structure D1:

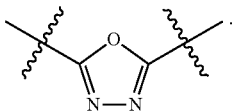

Also in Compound IV, X is CH$_2$ or S.

Further in Compound IV, Y is hydrogen, hydroxy, alkoxy, substituted or unsubstituted amino, substituted or unsubstituted thio, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, Y is substituted or unsubstituted phenyl. In some examples, Y is substituted or unsubstituted benzyl.

A fifth class of viral and/or fungal inhibitors comprises compounds represented by Compound V:

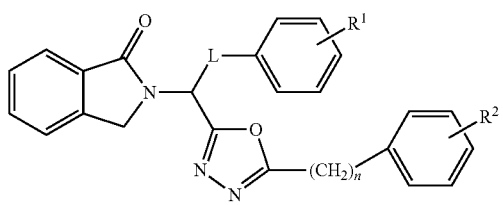

or pharmaceutically acceptable salts or prodrugs thereof.

In Compound V, n is 0 to 5. In some examples, n is 0.

Also in Compound V, L is substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{1-8}$heteroalkyl, substituted or unsubstituted C$_{2-8}$ heteroalkenyl, or substituted or unsubstituted C$_{2-8}$ heteroalkynyl. In some examples, L is (CH$_2$)$_m$ and m is 0 to 5. In some examples, m is 1.

Further in Compound V, R$^1$ and R$^2$ are each independently selected from hydrogen, halogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, R$^1$ is H. In some examples, R$^2$ is Cl.

An example of Compound V is as follows:

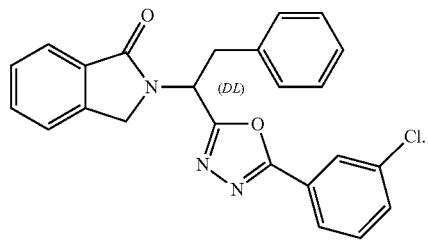

A sixth class of viral and/or fungal inhibitors comprises compounds represented by Compound VI:

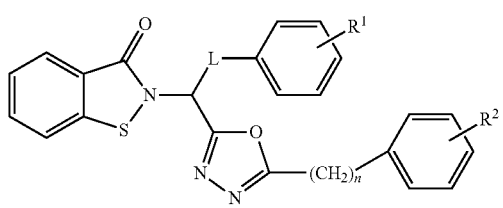

or pharmaceutically acceptable salts or prodrugs thereof.

In Compound VI, n is 0 to 5. In some examples, n is 0 or 1.

Also in Compound VI, L is substituted or unsubstituted C$_{1-8}$ alkyl, substituted or unsubstituted C$_{2-8}$ alkenyl, substituted or unsubstituted C$_{2-8}$ alkynyl, substituted or unsubstituted heteroalkyl, substituted or unsubstituted heteroalkenyl, or substituted or unsubstituted heteroalkynyl. In some examples, L is (CH$_2$)$_m$ and m is 0 to 5. In some examples, m is 1.

Additionally in Compound VI, R$^1$ and R$^2$ are each independently selected from hydrogen, halogen, substituted or unsubstituted C$_{1-12}$ alkyl, substituted or unsubstituted C$_{1-12}$haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, R$^1$ is H. In some examples, R$^2$ is H, F, or Cl.

Further examples of Compound VI are as follows:

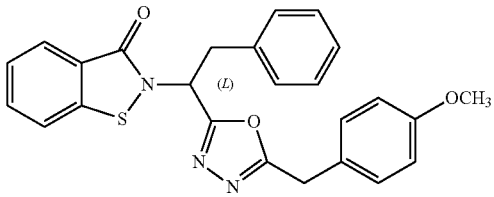

-continued

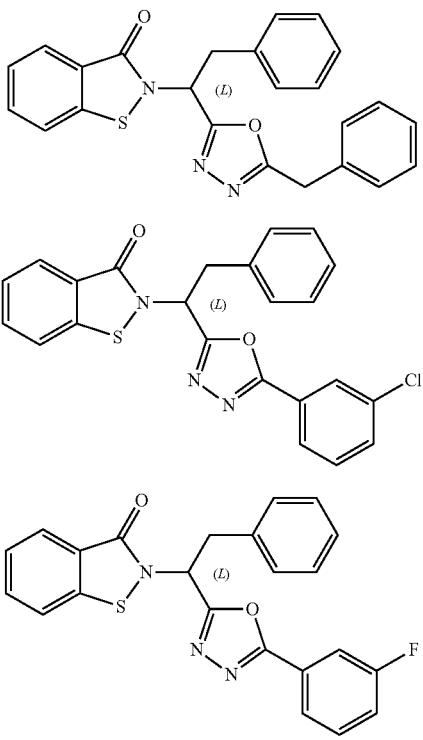

VI-2

VI-3

VI-4

A seventh class of viral and/or fungal inhibitors comprises compounds represented by Compound VII:

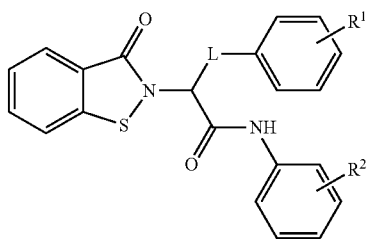

VII or pharmaceutically acceptable salts or prodrugs thereof.

In Compound VII, L is substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{1-8}$ heteroalkyl, substituted or unsubstituted $C_{2-8}$ heteroalkenyl, or substituted or unsubstituted $C_{2-8}$ heteroalkynyl. In some examples, L is $(CH_2)_m$ and m is 0 to 5. In some examples, m is 1. In some examples, —$CH_2CH_2C(O)OCH_2Ph$-.

Also in Compound VII, $R^1$ and $R^2$ are each independently selected from hydrogen, halogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, $R^1$ is H. In some examples, $R^2$ is OPh.

Further examples of Compound VII include Compound I-29, Compound I-30, Compound I-31, and Compound I-32.

An eighth class of viral and/or fungal inhibitors comprises compounds represented by Compound VIII:

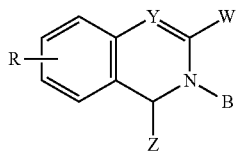

VIII or pharmaceutically acceptable salts or prodrugs thereof.

In Compound VIII, B is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl.

Also in Compound VIII, R is hydrogen, halogen, hydroxy, alkoxy, nitro, substituted or unsubstituted sulfonyl, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl.

Additionally, in Compound VIII, W is substituted or unsubstituted carbonyl, substituted or unsubstituted imino, substituted or unsubstituted thiocarbonyl, or substituted or unsubstituted thio. In some examples, W is a substituted or unsubstituted amidine or a substituted or unsubstituted carbamyl.

Further, in Compound VIII, Y is N or $CR^1$, wherein $R^1$ is hydrogen, halogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl.

Also, in Compound VIII, Z is =O, =S, =$NR^2$, or —$NR^3R^4$, wherein $R^2$, $R^3$, and $R^4$ are each independently selected from hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl.

Further, in Compound VIII, if B is —CH$_2$—CH$_3$, W is not

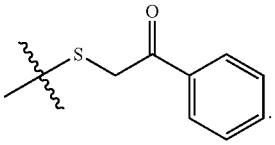 [SMILES: *SCC(=O)c1ccccc1]

A ninth class of viral and/or fungal inhibitors comprises compounds represented by Compound IX:

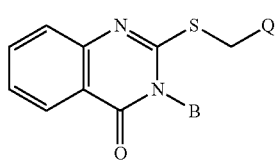

or pharmaceutically acceptable salts or prodrugs thereof.

In Compound IX, B is hydrogen, hydroxy, alkoxy, substituted or unsubstituted amino, substituted or unsubstituted thio, substituted or unsubstituted C$_{1-12}$ alkyl, substituted or unsubstituted C$_{1-12}$ heteroalkyl, substituted or unsubstituted C$_{2-12}$ alkenyl, substituted or unsubstituted C$_{2-12}$ heteroalkenyl, substituted or unsubstituted C$_{2-12}$ alkynyl, or substituted or unsubstituted C$_{2-12}$ heteroalkynyl, substituted or unsubstituted C$_{3-12}$ cycloalkyl, substituted or unsubstituted C$_{3-12}$ heterocycloalkyl, C$_{6-12}$ substituted or unsubstituted aryl, or substituted or unsubstituted C$_{5-12}$ heteroaryl. In one example, B is a hydrogen. In some examples, B is unsubstituted or substituted amino. Examples of substituted amino groups include substituted or unsubstituted sulfonamides, substituted or unsubstituted carbonyls, and substituted or unsubstituted amidos.

Also in Compound IX, Q is —C(O)R$^1$, —C(O)OR$^2$, —C(O)NHR$^2$, —C(O)NHSO$_2$R$^1$, —C(O)NHNHR$^3$,

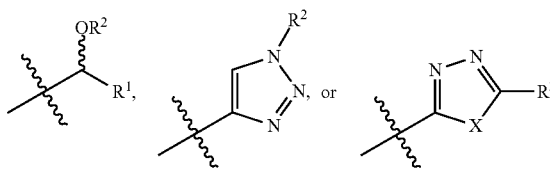

In these Q groups, R$^1$ is substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; R$^2$ is hydrogen or R$^1$; R$^3$ is R$^2$, —C(O)R$^1$, or —C(O)OR$^2$; and X is O or S.

Further, in Compound IX, if B is —CH$_2$—CH$_3$, Q is not

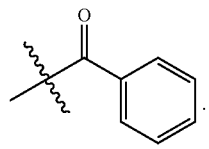 [SMILES: *C(=O)c1ccccc1]

The -Q group of Compound IX can have, for example, one of the following Structures E1-E8:

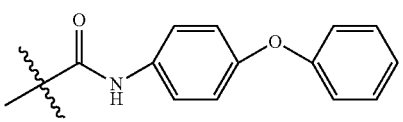
E1

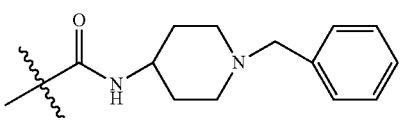
E2

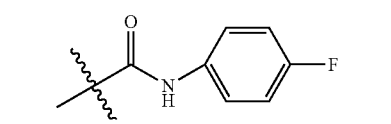
E3

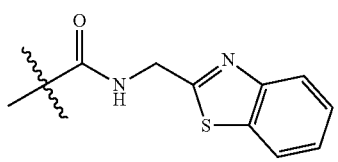
E4

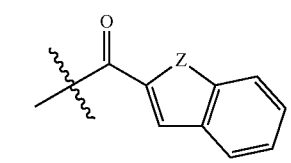
E5 wherein Z is O, S, or NH.

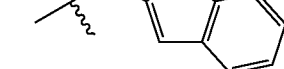
E6 wherein X is F or —OCH$_3$.

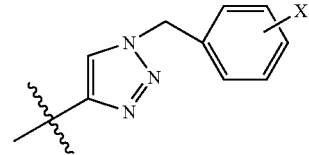
E7

E8
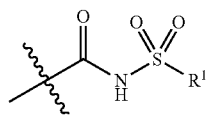
wherein R¹ is as defined above for Compound IX.
E9
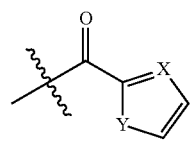
wherein X is CH or N and Y is O, NH, or S.
E10
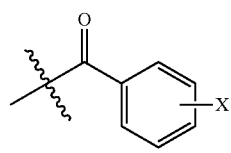
wherein X is F or —OCH₃. In some examples, fluoro is in the meta position. In some examples, fluoro is in the para position.
Further examples of Compound IX are as follows:
IX-1
IX-2
IX-3
IX-4
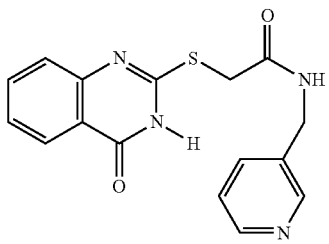
IX-5
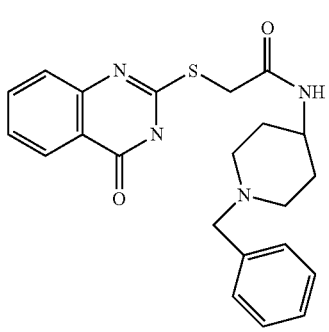
IX-6
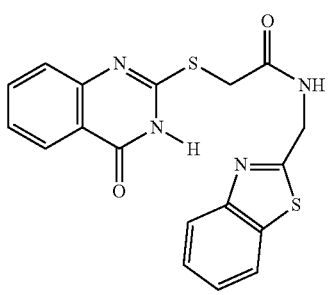
IX-7
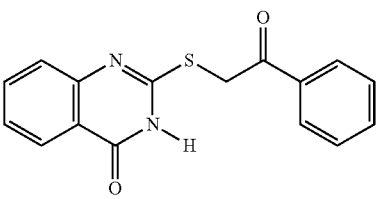
IX-8
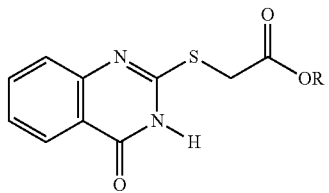
In Compound IX-8, R can be, for example, hydrogen, —CH₃, or tert-butyl.

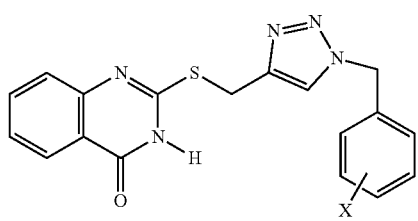

IX-9

In Compound IX-9, X can be, for example, meta-fluorine or para-OCH$_3$.

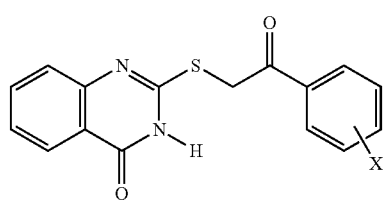

IX-10

In Compound IX-10, X can be, for example, fluorine, chlorine, —OCH$_3$, or phenyl (in the meta- or para-position).

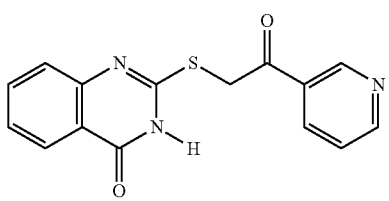

IX-11

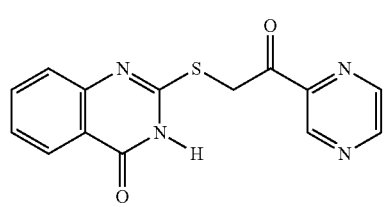

IX-12

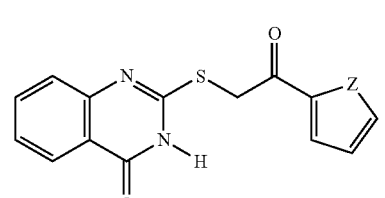

IX-13

In Compound IX-13, Z can be, for example, oxygen, sulfur, or NH.

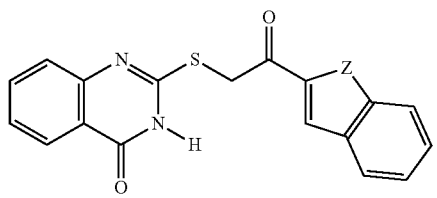

IX-14

In Compound IX-14, Z can be, for example, oxygen, sulfur, or NH.

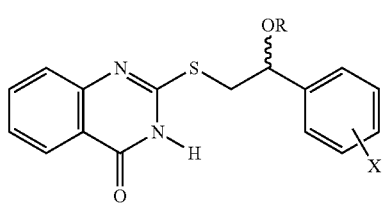

IX-15

In Compound IX-15, R can be, for example, hydrogen or —C(O)NH (CH$_2$)$_2$Ph; and X can be, for example, fluorine, chlorine, —OCH$_3$, or phenyl (in the meta- or para-position).

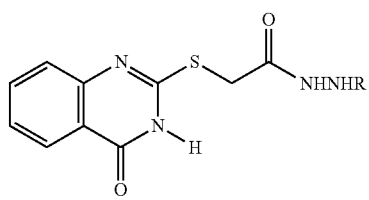

IX-16

In Compound IX-16, R can be, for example, hydrogen, —COO(t-butyl), —COO(benzyl), —CO(Aryl), —COH, —COCOO(t-butyl), —COCOO(benzyl), —SO$_2$(Aryl), —SO$_2$H, —SO$_2$COO(t-butyl), —SO$_2$COO(benzyl), —CONH(Aryl), —CONH$_2$, —CONHCOO(t-butyl), or —CONHCOO(benzyl).

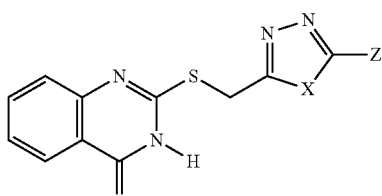

IX-17

In Compound IX-17, X can be, for example, oxygen or sulfur; and Z can be, for example, —COOH, —COOCH$_3$, —COO(CH$_2$)$_n$CH$_3$, or —COO(Aryl).

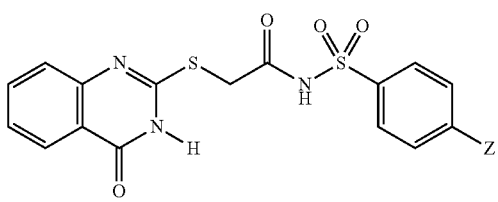

IX-18

In Compound IX-18, Z can be, for example, Cl or —OH.

A tenth class of viral and/or fungal inhibitors comprises compounds represented by Compound X:

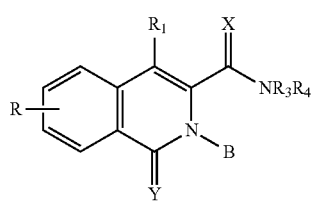

X or pharmaceutically acceptable salts or prodrugs thereof.

In Compound X, B is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl. In one example, B is H.

Also, in Compound X, R is hydrogen, halogen, hydroxy, alkoxy, nitro, substituted or unsubstituted sulfonyl, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, or substituted or unsubstituted $C_{5-12}$ heteroaryl. In one example, R is H.

Additionally, in Compound X, $R^1$ is hydrogen, halogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl. In one example, $R^1$ is H. In another example, $R^1$ is Br.

Also, in Compound X, $R^3$ and $R^4$ are each independently selected from hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl. In one example $R^3$ is H.

Further, in Compound X, X and Y are each independently selected from O, S, and $NR^2$, wherein $R^2$ is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ heteroalkyl, substituted or unsubstituted $C_{2-12}$ alkenyl, substituted or unsubstituted $C_{2-12}$ heteroalkenyl, substituted or unsubstituted $C_{2-12}$ alkynyl, or substituted or unsubstituted $C_{2-12}$ heteroalkynyl, substituted or unsubstituted $C_{3-12}$ cycloalkyl, substituted or unsubstituted $C_{3-12}$ heterocycloalkyl, $C_{6-12}$ substituted or unsubstituted aryl, and substituted or unsubstituted $C_{5-12}$ heteroaryl. In one example, X is O and Y is O.

The $R^4$ group of Compound X can have, for example, one of the following Structures F1-F10:

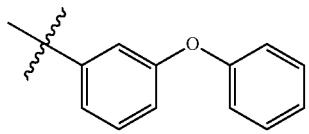

F1

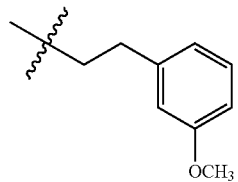

F2

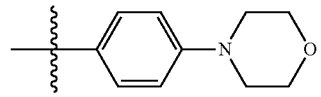

F3

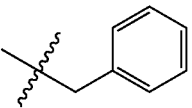

F4

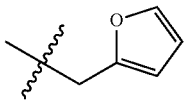

F5

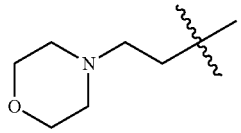

F6

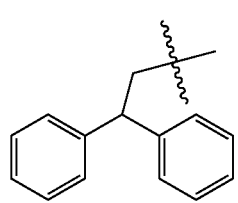

F7

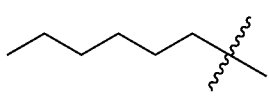 F8
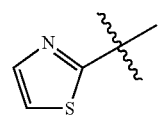 F9
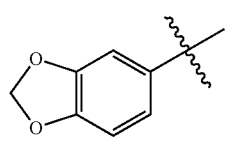 F10
In one example of Compound X, B is H, X is O, Y is O, R is H, $R^1$ is Br, $R^3$ is H, and $R^4$ is
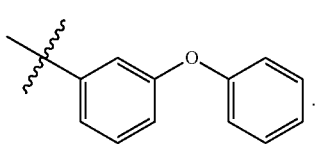 [SMILES: *c1cccc(Oc2ccccc2)c1]
Further examples of Compound X are as follows:
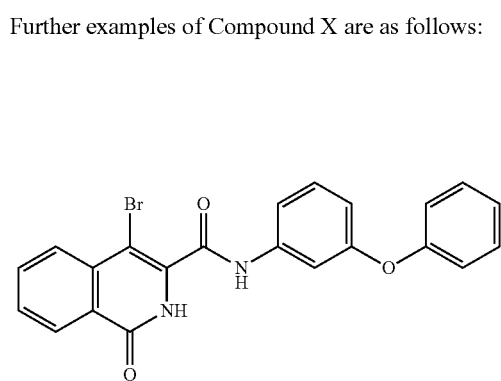 X-1
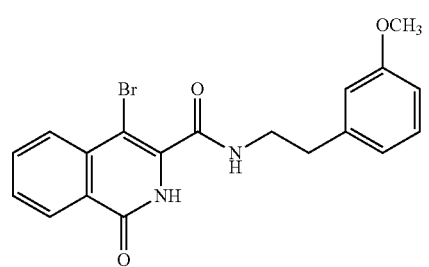 X-2
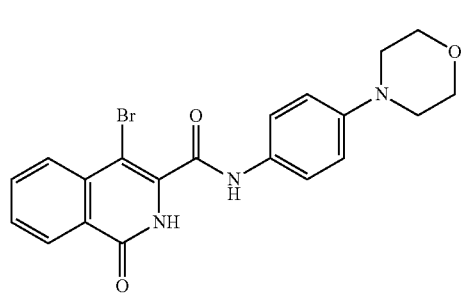 X-3
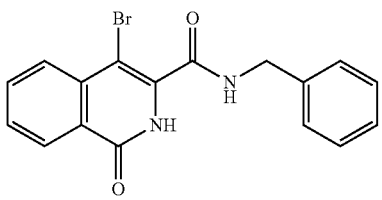 X-4
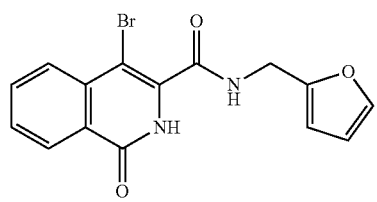 X-5
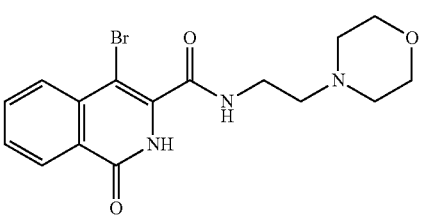 X-6
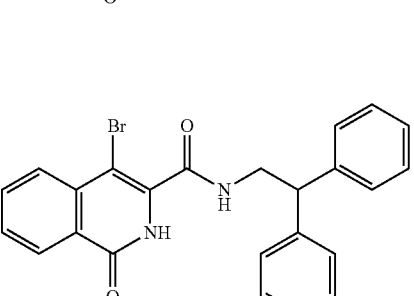 X-7
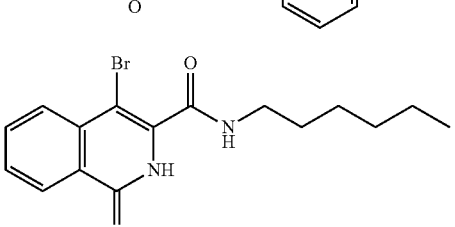 X-8
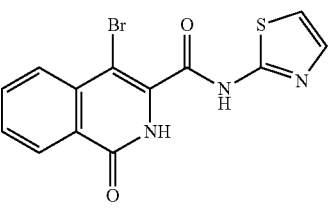 X-9
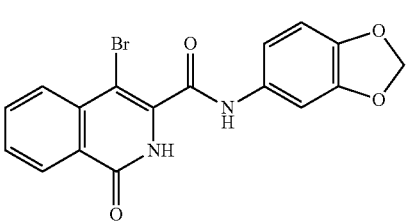 X-10

-continued

X-11 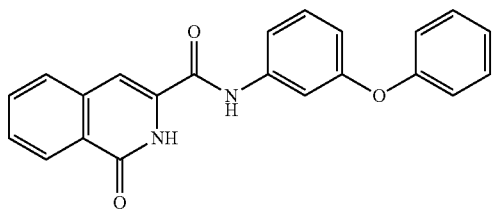

X-12 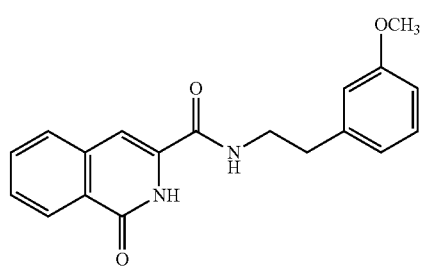

X-13 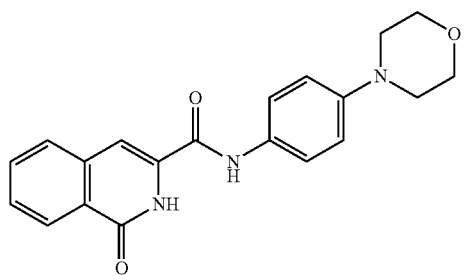

X-14 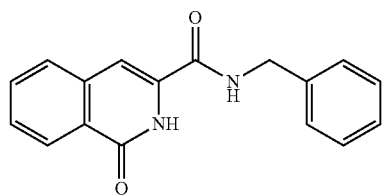

X-15 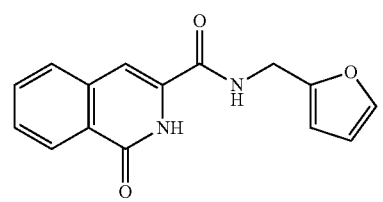

X-16 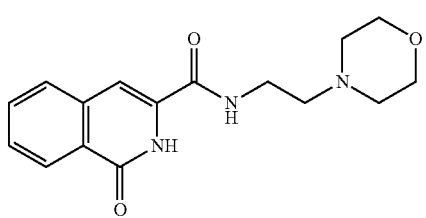

X-17 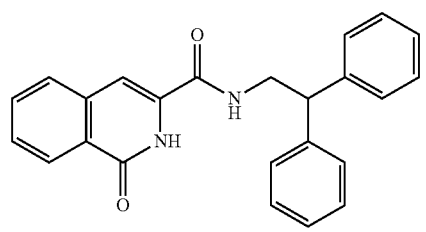

-continued

X-18 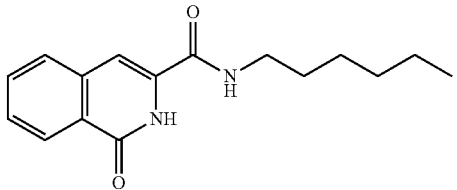

X-19 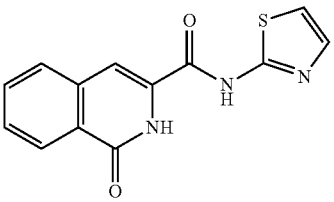

X-20 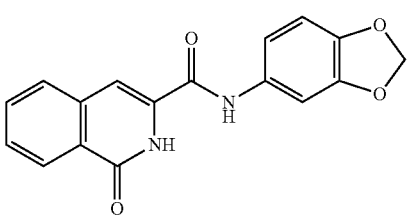

The compounds described herein may contain chiral centers. Such chiral centers may be of either the (R) or (S) configuration, or may be a mixture thereof. Thus, the compounds provided herein may be enantiomerically pure, or be stereoisomeric or diastereomeric mixtures. The separation of mixtures of optical isomers to obtain pure enantiomers is well known in the art and is contemplated. Enantiomeric resolution may, for example, be achieved by fractional crystallization of salts with chiral acids or by chromatographic separation on chiral columns.

In the case of amino acid residues, such residues may be of either the L- or D-form. As used herein, the term amino acid refers to α-amino acids which are racemic, or of either the D- or L-configuration. The designation "L" preceding an amino acid refers to the L-isomer of the amino acid. The designation "DL" preceding an amino acid designation refers to a mixture of the L- and D-isomers of the amino acid. The chiral centers of the compounds provided herein may undergo epimerization in vivo. As such, the administration of a compound in its (L) form is equivalent, for compounds that undergo epimerization in vivo, to administration of the compound in its (D) form.

The compounds described herein can be prepared in a variety of ways. The compounds can be synthesized using synthetic methods known in the art of synthetic organic chemistry or variations thereon as appreciated by those skilled in the art. The compounds described herein can be prepared from readily available starting materials. Optimum reaction conditions may vary with the particular reactants or solvent used, but such conditions can be determined by one skilled in the art by routine optimization procedures.

Variations on Compound I, Compound II, Compound III, Compound IV, Compound V, Compound VI, Compound VII, Compound VIII, Compound IX, and Compound X include the addition, subtraction, or movement of the various constituents as described for each compound. Similarly, when one or more chiral centers is present in a molecule the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4$^{th}$ Ed., Wiley & Sons, 2006, which is incorporated herein by reference in its entirety. The synthesis and subsequent testing of various compounds as described by Compound I, Compound II, Compound III, Compound IV, Compound V, Compound VI, Compound VII, Compound VIII, Compound IX, and Compound X to determine efficacy is contemplated.

Reactions to produce the compounds described herein can be carried out in solvents which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Examples of compounds described by Compound I, wherein R$^3$ of the X group includes an isoindolinone, and pharmaceutically acceptable salts and prodrugs thereof can be made using the methods shown in Scheme 1.

Scheme 1:

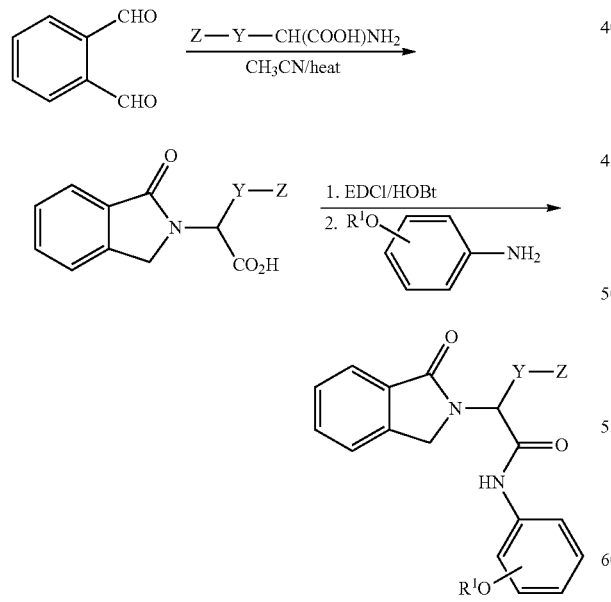

Examples of compounds described by Compound II, wherein Z is (C=O)AR$^6$, and pharmaceutically acceptable salts and prodrugs thereof can be made, for example, using the methods shown in Scheme 2.

Scheme 2:

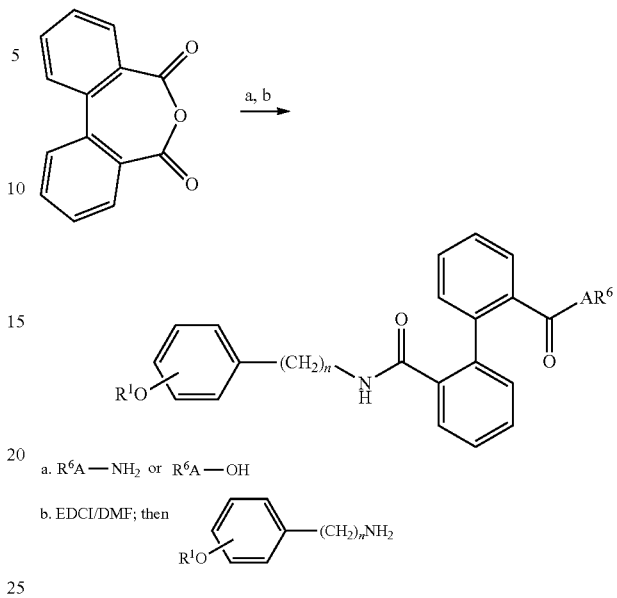

a. R$^6$A—NH$_2$ or R$^6$A—OH b. EDCI/DMF; then

Examples of compounds described by Compound III, wherein Y is NH, Q is —C(O)CH$_2$—, and Z is an aryl substituted thio, and pharmaceutically acceptable salts and prodrugs thereof can be made, for example, using the methods shown in Scheme 3.

Scheme 3:

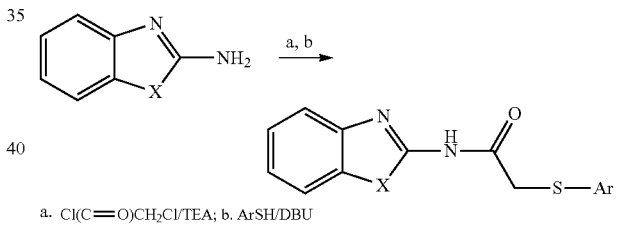

a. Cl(C=O)CH$_2$Cl/TEA; b. ArSH/DBU

Examples of compounds described by Compound IV, wherein X is S, W is —C(O)NR$^2$, and Y is H, and pharmaceutically acceptable salts and prodrugs thereof can be made, for example, using the methods shown in Scheme 4.

Scheme 4:

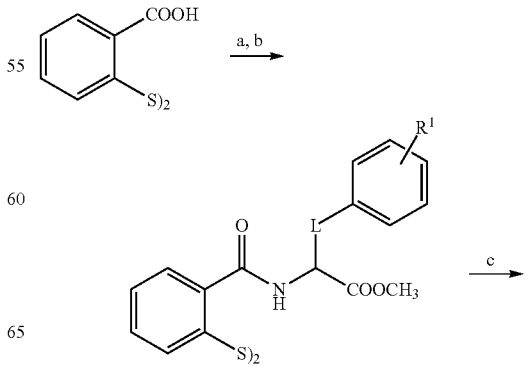

-continued

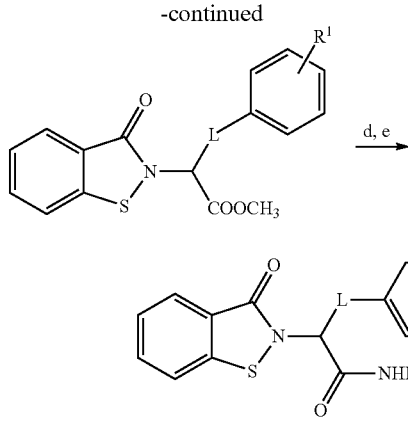

a. EDCI/DMF; b. (DL)NH₂CHL(Ph—R¹)COOCH₃/Et₃N
c. Br₂/Et₃N; d. LiOH, aq. dioxane; e. EDCI/DMF, then R²NH₂

Examples of compounds described by Compound V and pharmaceutically acceptable salts and prodrugs thereof can be made, for example, using the methods shown in Scheme 5.

Scheme 5:

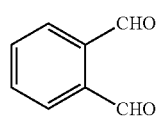

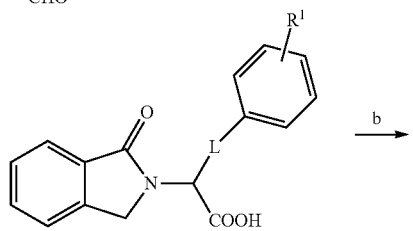

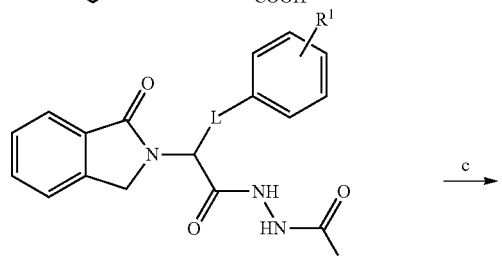

a. (DL)L(Ph—R¹)CH(COOH)NH₂
b. EDCI/DMF, then NH₂NH(C=O)
c. p-TsCl/Et₃N

Examples of compounds described by Compound VI and pharmaceutically acceptable salts and prodrugs thereof can be made, for example, using the methods shown in Scheme 6.

Scheme 6:

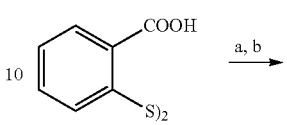

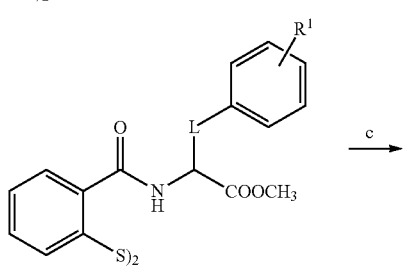

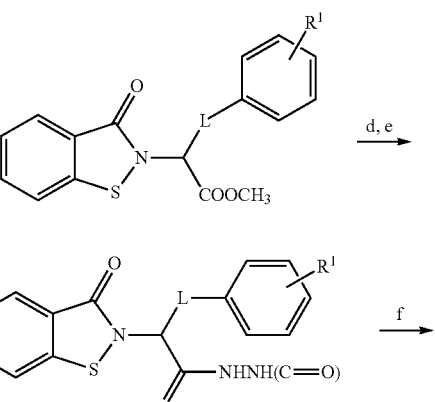

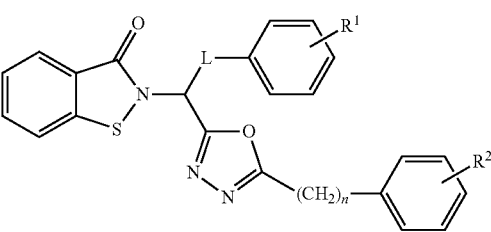

a. EDCI/DMF; b. (DL)NH₂CHL(Ph—R¹)COOCH₃/Et₃N
c. Br₂/Et₃N; d. LiOH, aq. dioxane; e. EDCI/DMF, then
NH₂NH(C=O)(CH₂)ₙ—Ph—R¹); f. p-TsCl Examples of compounds described by Compound VII, wherein n is 1, and pharmaceutically acceptable salts and prodrugs thereof can be made, for example, using the methods shown in Scheme 7.

Scheme 7:

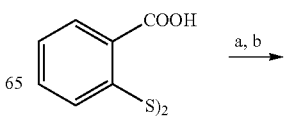

-continued

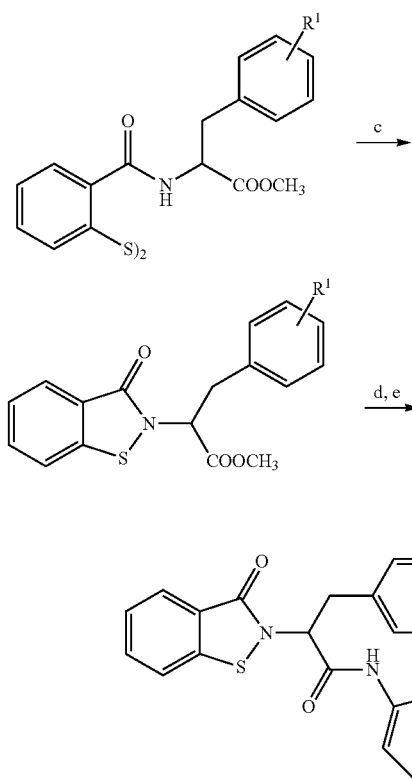

a. EDCI/DMF; b. (DL)NH₂CHCH₂(Ph—R¹)COOCH₃
c. Br₂/Et₃N; d. LiOH, aq. dioxane; e. EDCI/DMF, then
NH₂Ph—R²

Examples of compounds described by Compound VIII, wherein Y is N, B is H, W is —SCH₂(C=O)NHR¹, R is H, and Z is =O, and pharmaceutically acceptable salts and prodrugs thereof can be made, for example, using the methods shown in Scheme 8. In Scheme 8, T represents a substitution group as described herein.

Scheme 8:

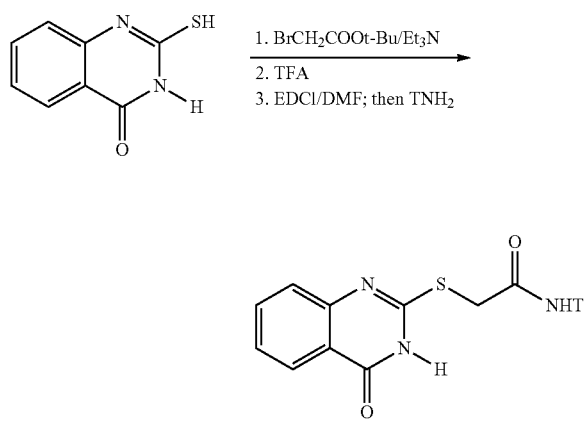

Examples of compounds described by Compound IX, wherein Q is a substituted or unsubstituted carbonyl, and pharmaceutically acceptable salts and prodrugs thereof can be made, for example, using the methods shown in Scheme 9.

Scheme 9:

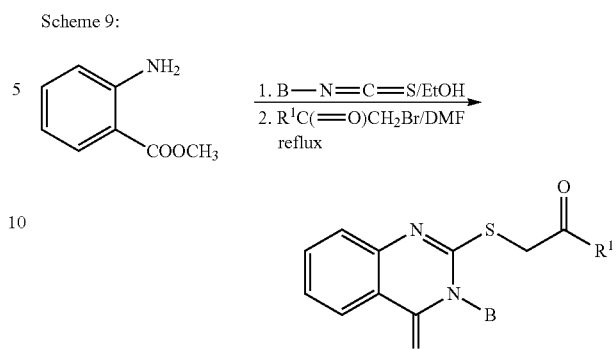

A method of making examples of compounds described by Compound IX, wherein Q is a substituted or unsubstituted carbonyl and B is a substituted or unsubstituted amino group, and pharmaceutically acceptable salts and prodrugs thereof is shown in Scheme 10. In Scheme 10, T represents a substitution group as described herein.

Scheme 10:

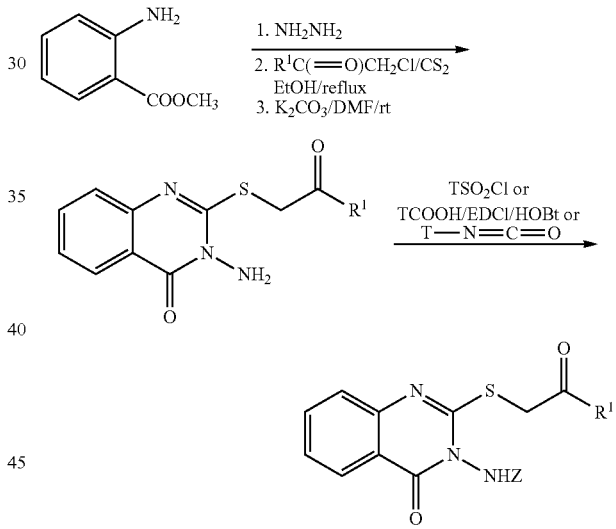

Z = SO₂T, TC(=O), TNHC(=O)

A method of making examples of compounds described by Compound IX, wherein Q is a substituted or unsubstituted amino and B is hydrogen, and pharmaceutically acceptable salts and prodrugs thereof is shown in Scheme 11.

Scheme 11:

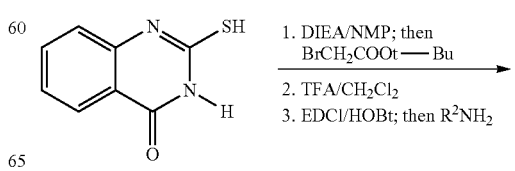

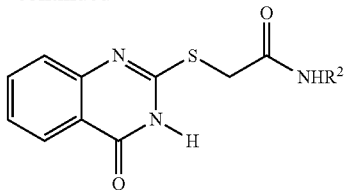

Examples of compounds described by Compound X and pharmaceutically acceptable salts and prodrugs thereof can be made, for example, using the methods shown in Scheme 12.

Scheme 12:

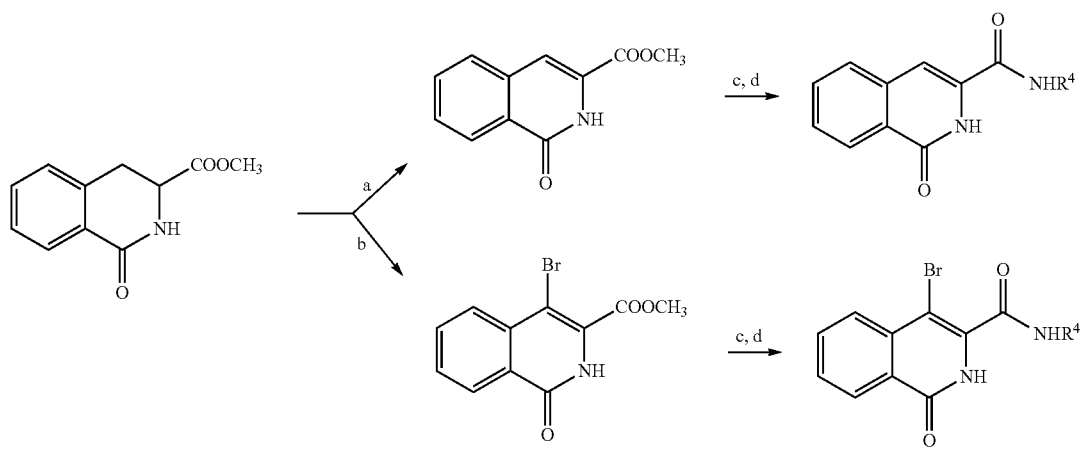

[a]DDQ/1,4-dioxane/reflux; [b]NBS/dibenzoyl peroxide/DCM;
[c]1M LiOH/RT/1 h; [d]EDCI/DMF then $R^4NH_2$ The compounds described herein or pharmaceutically acceptable salts or prodrugs thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the compounds described herein or a pharmaceutically acceptable salt or prodrug thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected substrate without causing significant undesirable biological effects or interacting in a deleterious manner with any of the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compounds described herein or pharmaceutically acceptable salts or prodrugs thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration of the compounds described herein or a pharmaceutically acceptable salt or prodrug thereof include capsules, tablets, pills, powders, and granules. In such solid dosage forms, the compounds described herein or a pharmaceutically acceptable salt or prodrug thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting, emulsifying, suspending, sweetening, flavoring, or perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are preferably suppositories which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, and inhalants. The compounds described herein or pharmaceutically acceptable salts or prodrugs thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of the compounds described herein that are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Berge et al., J. Pharm. Sci. (1977) 66:1-19, which is incorporated herein by reference in its entirety, at least, for compositions taught herein.)

The compounds and compositions described above are useful in treating viral and fungal infections in humans, e.g., including pediatric and geriatric populations, and animals, e.g., veterinary applications. Methods of using the compounds and compositions described herein comprise administering to a subject a therapeutically effective amount of the compounds or compositions described herein or a pharmaceutically acceptable salt or prodrug thereof. Viral infections include, for example, Hepatitis C Virus and *Flavivirus* infections. *Flavivirus* infections include, for example, West Nile Virus, Dengue Virus, and Japanese Encephalitis Virus. Several serotypes of Dengue Virus have been identified such as, for example, serotype DEN-1, serotype DEN-2, serotype DEN-3, and serotype DEN-4. Examples of fungal infections treatable by the methods described herein include fluconazole resistant fungal infections and fungal infections caused by the genus *Candida* (e.g., candidiasis, including vaginal candidiasis and hospital acquired candidiasis). The methods described herein are useful in treating fungal infections caused by several species of *Candida*, including *Candida albicans, Candida glabrata*, and *Candida tropicalis*. The methods described herein are also useful in treating *Saccharomyces cervisiae* infections. Further, the methods of treating fungal infections as described herein are useful in treating immunocompromised subjects. Immunocompromised subjects include, for example, HIV-positive subjects; subjects undergoing immunotherapy; cancer patients; individuals with viral infections; individuals with an autoimmune disease; patients with malignancies, leukemias, collagen-vascular diseases, or congenital or acquired immunodeficiency; organ-transplant recipients receiving immunosuppressive therapy; and other patients receiving immunosuppressive therapy. As used herein the term treating or treatment includes prevention; delay in onset; diminution, eradication, or delay in exacerbation of signs or symptoms after onset; and prevention of relapse.

The methods and compounds or compositions as described herein are useful for both prophylactic and therapeutic treatment of viral and fungal infections. For prophylactic use, a therapeutically effective amount of the compounds or compositions described herein are administered to a subject prior to exposure (e.g., before or when traveling to a location where viral or fungal infections are possible), during a period of potential exposure to viral or fungal infections, or after a period of potential exposure to viral or fungal infections. Prophylactic administration can occur for several days to weeks prior to potential exposure, during a period of potential exposure, and for a period of time, e.g., several days to weeks, after potential exposure. Therapeutic treatment involves administering to a subject a therapeutically effective amount of the compounds or compositions described herein after a viral or fungal infection is diagnosed.

Administration of compounds or compositions described herein or pharmaceutically acceptable salts or prodrugs thereof can be carried out using therapeutically effective amounts of the compounds or compositions described herein or pharmaceutically acceptable salts or prodrugs thereof for periods of time effective to treat viral or fungal infections. The effective amount of the compounds or compositions described herein or pharmaceutically acceptable salts or prodrugs thereof may be determined by one of ordinary skill in the art, and includes exemplary dosage amounts for a mammal of from about 0.05 to about 100 mg/kg of body weight of active compound per day, which may be administered in a single dose or in the form of individual divided doses, such as from 1 to 4 times per day. Alternatively, the dosage amount can be from about 0.05 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In these methods, a viral or fungal infection, for example, can be further treated with one or more additional agents. For example, the methods of treating and preventing viral or fungal infections as described herein can further include administering a second compound or composition to the subject. In the treatment of viral infections, the second compound or composition can include an antiviral compound or mixtures of antiviral compounds (e.g., pegylated interferon-α, ribavirin, and mixtures thereof). The second compound or composition used in the treatment of fungal infections can include antifungal compounds, antiviral compounds, or mixtures thereof. Examples of second compounds include triazole antifungals, thiazole antifungals, imidazole antifungals, polyene antifungals, enchinocandin antifungals, allylamine antifungals, and amphotericin B. Antiviral compounds that can be used in combination with the compounds described herein include, for example, nucleoside polymerase inhibitors, non-nucleoside polymerase inhibitors, protease inhibitors, nucleoside or nucleotide reverse transcriptase inhibitors, non-nucleoside reverse transcriptase inhibitors, entry inhibitors, assembly inhibitors, integrase inhibitors, kinase inhibitors, enzyme inhibitors, maturation inhibitors, M2 inhibitors, and neuraminidase inhibitors. Examples of such additional antiviral compounds include, but are not limited to amantadine, rimantadine, oseltamivir (Tamiflu®, Roche Laboratories, Nutley, N.J.), zanamivir (Relenza®, GlaxoSmithKline, Philadelphia, Pa.), peramivir, raltegravir, Maraviros, enfuvirtide, bevirimat, Vivecon™ (Myriad Genetics, Salt Lake City, Utah), Combivir® (zidovudine+lamivudine, AZT+3TC) (GlaxoSmithKline, Philadelphia, Pa.), Emtriva® (emtricitabine, FTC) (Gilead Sciences, Foster City, Calif.), Epivir® (lamivudine, 3TC) (GlaxoSmithKline, Philadephia, Pa), Epzicom® (Kivexa, abacavir+lamivudine, ABC+3TC) (GlaxoSmithKline, Philadelphia, Pa.), Retrovir® (zidovudine, AZT, ZDV) (GlaxoSmithKline, Philadelphia, Pa.), Trizivir® (abacavir+zidovudine+lamivudine, ABC+AZT+3TC) (GlaxoSmithKline, Philadelphia, Pa.), Truvada® (tenofovir DF+emtricitabine, TDF+FTC) (Gilead Sciences, Foster City, Calif.), Videx® & Videx EC® (didanosine, ddI) (Bristol-Myers Squibb, Princeton, N.J.), Viread® (tenofovir disoproxil fumarate, TDF) (Gilead Sciences, Foster City, Calif.), Zerit® (stavudine, d4T) (Bristol-Myers Squibb, Princeton, N.J.), Ziagen® (abacavir, ABC) (GlaxoSmithKline, Philadelphia, Pa.), Racivir™ (RCV) (Pharmasset, Princeton, N.J.), Amdoxovir™ (AMDX, DAPD) (RFS Pharma, Tucker, Ga.), apricitabine (SPD754, AVX754), elvucitabine (ACH-126, 443, Beta-L-Fd4C), Immunitin® (HE2000, alpha-epibromide) (Hollis-Eden Pharmaceuticals, San Diego, Calif.), Proleukin® (aldesleukin, Interleukin-2, IL-2) (Chiron Corporation, Emeryville, Calif.), Remune® (HIV-1 Immunogen, Salk vaccine) (Orchestra Therapeutics, Carlsbad, Calif.), BAY 50-4798, IR103, Intelence™ (etravirine, TMC-125) (Tibotec Therapeutics, Irvine, Calif.), Rescriptor® (delavirdine, DLV) (Pfizer, New York, N.Y.), Sustiva® (Stocrin, efavirenz, EFV) (Bristol-Myers Squibb, Princeton, N.J.), Viramune® (nevirapine, NVP) (Boehringer Ingelheim, Ridgefield, Conn.), rilpivirine (TMC-278), Agenerase® (amprenavir, APV) (GlaxoSmithKline, Philadelphia, Pa.), Aptivus® (tipranavir, TPV) (Boehringer Ingelheim, Ridgefield, Conn.), Crixivan® (indinavir, IDV) (Merck, Whitehouse Station, N.J.), Invirase® (saquinavir, SQV) (Roche Laboratories, Nutley, N.J.), Kaletra® (Aluvia®, lopinavir/ritonavir, LPV/r) (Abbott Laboratories, Abbott Park, Ill.), Lexiva® (Telzir®, fosamprenavir, FPV) (GlaxoSmithKline, Philadelphia, Pa.), Norvir® (ritonavir, RTV) (Abbott Laboratories, Abbott Park, Ill.), Prezista® (darunavir, DRV) (Tibotec Therapeutics, Irvine, Calif.), Reyataz® (atazanavir, ATV) (Bristol-Myers Squibb, Princeton, N.J.), Viracept® (nelfinavir, NFV) (Pfizer, Inc., New York, N.Y.), Fuzeon® (enfuvirtide, ENF, T-20) (Roche Laboratories, Inc., Nutley, N.J.), Selzentry® (Celsentri®, maraviroc, UK-427,857) (Pfizer, Inc., New York, N.Y.), Vicriviroc® (SCH-417690, SCH-D) (Schering-Plough, Kenilworth, N.J.), PRO 140 (Progenics Pharmaceuticals, Tarrytown, N.Y.), TNX-355 (Tanox, Inc., Houston, Tex.), Isentress® (raltegravir, MK-0518) (Merck, Whitehouse Station, N.J.), Elvitegravir™ (GS-9137) (Gilead Sciences, Foster City, Calif.), Bevirimat™ (PA-457) (Panacos Pharmaceuticals, Inc., Watertown, Mass.), and Droxia® or Hydrea® (hydroxyurea, HU) (Bristol-Myers Squibb, Princeton, N.J.).

The one or more additional agents and the compounds or compositions described herein or a pharmaceutically acceptable salt or prodrug thereof can be administered in any order, including simultaneous administration, as well as temporally spaced order of up to several days apart. The methods may also include more than a single administration of the one or more additional agents and/or the compounds or compositions described herein or a pharmaceutically acceptable salt or prodrug thereof. The administration of the one or more additional agent and the compounds or compositions described herein or a pharmaceutically acceptable salt or prodrug thereof may be by the same or different routes and concurrently or sequentially.

The examples below are intended to further illustrate certain aspects of the methods, compounds, and compositions described herein, and are not intended to limit the scope of the claims.

EXAMPLES

Example 1

Expression of WNV in *E. coli* and Purification

Procedures for expression and purification of WNV (EG101 strain) were similar to those described elsewhere by *Mueller* et al., Int. J. Biochem. Cell. Biol., 39: 606-14 (2007). Briefly, *E. coli* Top10 F' cells (Invitrogen, Carlsbad, Calif.) were transformed with the protease expression plasmid. Cells were grown at 37° C. until the $OD_{600}$ was ~0.5. Cells were then induced with isopropyl-1-thio-β-D-galactopyranoside (American Bioanalytical, Natick, Mass.) (0.5 mM), and incubated for 4 h at 37° C. Cells were harvested by centrifugation (5000×g) for 15 min at 4° C., washed once with a buffer containing 50 mM Tris-HCl, pH 7.5, and 200 mM NaCl, centrifuged at 5000×g for 15 min at 4° C., and stored at −80° C. until used.

Proteases were purified by suspending bacterial pellets in 50 mM Hepes, pH 7.0, 500 mM NaCl, (buffer A) with 0.05 mg/ml lysozyme. Cells were incubated for 30 min on ice after addition of 10% stock solution of Triton X-100 (final concentration of 0.5%). Cells were disrupted by sonication for 2 min and the soluble fraction was collected after centrifugation (15,000×g) for 30 min at 4° C. The soluble fraction was incubated for 1 h at 4° C. with Talon resin (BD Bioscience, San Jose, Calif.) which was pre-equilibrated in buffer A. The affinity resin was centrifuged at (400×g) for 10 min at 4° C., washed three times with buffer A, and packed into a column. Washing of the column was continued with the buffer A containing 10 mM imidazole, followed by elution of the protease with buffer A containing 150 mM imidazole. The protease was concentrated and further purified by Sephadex G-75 gel filtration chromatography. The purified protease fractions were pooled and dialyzed against a buffer containing 50 mM Tris-HCl pH 7.5 and 300 mM NaCl (4×1L). Aliquots (100 μl) were frozen at −80° C.

Example 2

Analysis of Protease Inhibitor Compounds

Compounds I-1 to I-14 and II-1 to II-4 (which were synthesized using methods of organic synthesis as discussed above) were analyzed by in vitro protease assays performed in opaque 96-well plates. The enzyme kinetics was done under steady-state conditions. The standard reaction mixtures (50 μL) containing 200 mM Tris-HCl, pH 9.5, 6 mM NaCl, 30% glycerol, 67 nM of WNV protease and 50 μM inhibitor in each assay were incubated for 15 min at room temperature. Reactions were started by the addition of the substrate Boc-Gly-Lys-Arg-AMC at 100 μM final concentration and incubated at room temperature for 15 min. The absorbance of each well containing para-nitroaniline was measured at 405 nm using a spectrophotometer (Molecular Devices, Sunnyvale, Calif.); the fluorescence of AMC released from the WNV substrate was measured using a Tecan Geneios (Durham, N.C.) spectrofluorometer at excitation and emission wavelengths of 390 nm and 420 nm, respectively. Similarly, the WNV protease activity was also determined using the fluorogenic tetrapeptide substrate containing the P4-P1 residues and the fluorogenic group, 4-methoxy-β-naphthylamide (MNA), at P1' position (Z-Val-Lys-Lys-Arg-MNA) (SEQ ID NO:1). Fluorescence was measured using a spectrofluorometer (Molecular Devices) at excitation and emission wavelengths of 290 and 420 nm, respectively. Fluorescence values obtained with no inhibitor control were taken as 100% and those in the presence of inhibitors were plotted as the percent inhibition of the control.

As shown in FIGS. 1-4, Compounds I-1 to I-14 and II-1 to II-4 inhibit WNV protease activity. Further, many of the compounds inhibit WNV protease activity at a greater than 70% level. The structures of Compounds I-1 to I-14 and II-1 to II-4 are provided above.

Compounds I-2, I-4, I-6, I-7, I-8, I-9, I-23, I-26, I-27, I-28, I-29, I-30, I-31, I-32, III-1, III-2, VI-1, VI-2, VI-3, and VI-4 were also tested for WNV protease inhibition activity according to the procedure detailed above. Further, Compounds I-28, V-1, VI-2, VI-3, VI-4, and IX-1 were tested for DENV protease inhibition activity. The activity data for the compounds are shown in Table 1 and FIGS. 5-7. The structures of Compounds I-2, I-4, I-6, I-7, I-8, I-9, I-23, I-26, I-27, I-28, I-29, I-30, I-31, I-32, III-1, III-2, VI-1, VI-2, VI-3, VI-4, and IX-1 are provided above.

TABLE 1

Protease Inhibition Activity

| Compound | $IC_{50}$ (μM) WNVpro | $IC_{50}$ (μM) DENVpro |
|---|---|---|
| I-2 | 11.1 | N/A |
| I-4 | 19.7 | N/A |
| I-6 | 22.1 | N/A |
| I-7 | 26.1 | N/A |
| I-8 | 22.9 | N/A |
| I-9 | 31.2 | N/A |
| I-23 | 38.6 | N/A |
| I-26 | 13.0 | N/A |
| I-27 | 22.7 | N/A |
| I-28 | 15.5 | 45.0 |
| I-29 | 9.0 | N/A |
| I-30 | 6.0 | N/A |
| I-31 | 2.6 | N/A |
| I-32 | 6.6 | N/A |
| III-1 | 14.7 | N/A |
| III-2 | 34.1 | N/A |
| V-1 | N/A | 12.2 |
| VI-1 | 26.0 | N/A |
| VI-2 | 2.1 | 9.6 |
| VI-3 | 7.6 | 10.6 |
| VI-4 | 9.8 | 11.4 |
| IX-1 | N/A | 89 |

Example 3

Analysis of Protease Inhibitor Compounds

Compounds V-1, V-2, V-3, V-4, V-5, V-14, and V-15 (which were synthesized using methods of organic synthesis as shown below in Example 4) were analyzed by in vitro protease assays as described in Example 2 above using the following modifications. The protease inhibitor assays contained 200 mM Tris-HCl buffer, pH 9.5, 13.5 mM NaCl, 30% glycerol, 0.025 µM enzyme (2.5 µmol), 100 µM fluorogenic peptide substrate, and 50 µM inhibitor. The inhibitors were dissolved in DMSO and diluted in assay buffer. The DMSO concentration in the assay mix was maintained at 1%, including in the no-inhibitor control. The assay mixtures containing WNV protease with an inhibitor (or without the inhibitor as a control) were pre-incubated at room temperature for fifteen minutes. An aliquot of the substrate (100 µM) was added and the incubation continued for an additional fifteen minutes. Fluorescence values were obtained using excitation and emission wavelengths of 385 nm and 465 nm, respectively. The percent inhibition of protease activity was determined using Microsoft EXCEL (Microsoft; Redmond, Wash.). For calculation of $IC_{50}$ value, in vitro protease assays were performed in triplicate as described above in the presence of 10, 20, 30, 40 and 50 µM of the compounds or without the compound. The % inhibition (y-axis) was plotted against the concentration of the inhibitor (x-axis) using GraphPad Prism 5.0 software (San Diego, Calif.).

Figure 8:
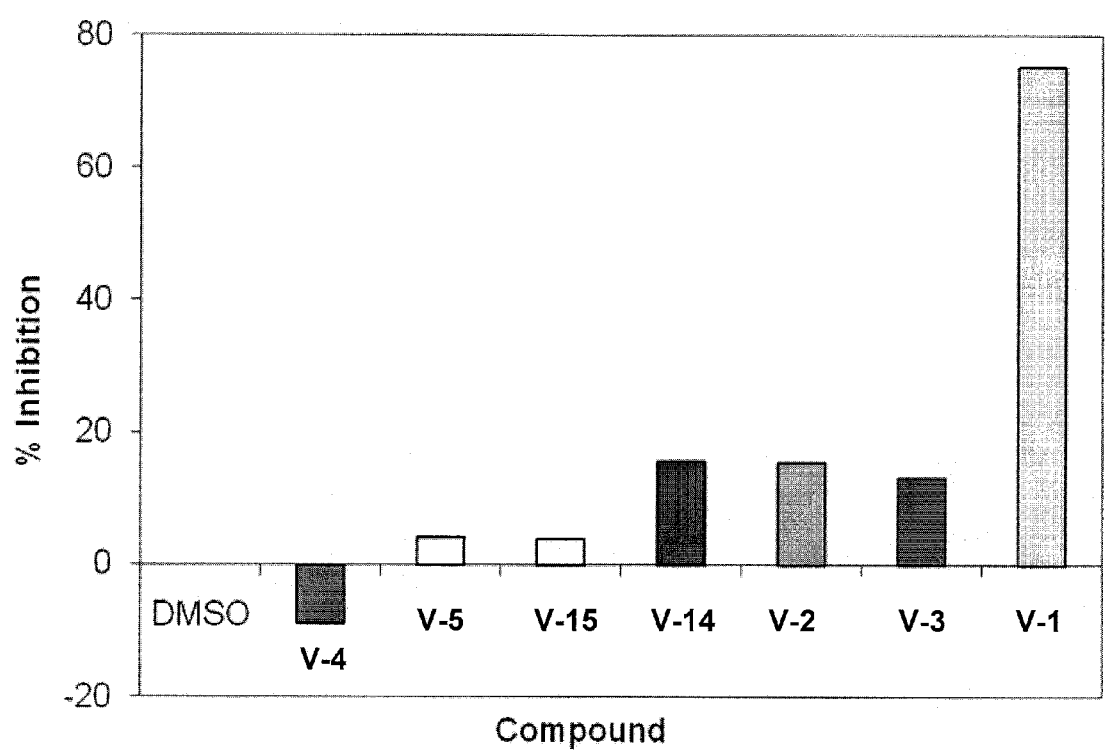
FIG. 8 is a chart showing percent inhibition of West Nile Virus protease by compounds V-1, V-2, V-3, V-4, V-5, V-14, and V-15 compared to DMSO (1%) control.

As shown in FIG. 8, Compounds V-1, V-2, V-3, V-5, V-14, and V-15 inhibit WNV protease activity. Compound V-4 did not display WNV protease inhibition in the assay performed.

Example 4

Synthesis of Compounds

General:

The $^1$H NMR spectra were recorded on a Varian XL-300 or XL-400 NMR spectrometer (Varian, Inc.; Palo Alto, Calif.). Melting points were determined on a Mel-Temp apparatus (Laboratory Devices; Cambridge, Mass.) and are uncorrected. Reagents and solvents were purchased from various chemical suppliers (Aldrich, St. Louis, Mo.; Acros Organics, Geel, Belgium; TCI America, Portland, Oreg.; and Bachem, Bubendorf, Switzerland). Silica gel (230-450 mesh) used for flash chromatography was purchased from Sorbent Technologies (Atlanta, Ga.). Thin layer chromatography was performed using Analtech silica gel plates (Analtech; Newark, Del.). The TLC plates were visualized using iodine and/or UV light.

Synthesis of Starting Material 1:

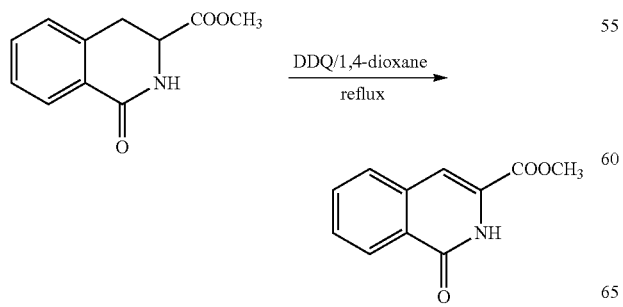

To a solution of compound 1-Oxo-1,2,3,4-tetrahydroisoquinoline 3-carboxymethyl ester (13.61 g; 66 mmol) in 200 mL of 1,4-dioxane was added 2,3-dichloro-5,6-dicyanobenzoquinone (DDQ) (16.0 g; 70.5 mmol). The resultant mixture was refluxed overnight. After the reaction was complete, the solvent was removed. The residue was taken up with 200 mL ethyl acetate and washed with 5% NaOH (2×50 mL). The organic layer was dried over anhydrous sodium sulfate. The drying agent was filtered and the filtrate was evaporated. The crude product was purified with flash chromatography (silica gel/ethyl acetate/hexanes) to give the product (starting material 1) as a white solid (3.0 g; 22%), mp 154-155° C. $^1$H NMR (CDCl$_3$): 3.92 (s, 3H), 7.52-7.68 (m, 4H), 8.37-8.41 (m, 1H), 9.12 (s, 1H).

Synthesis of Starting Material 2:

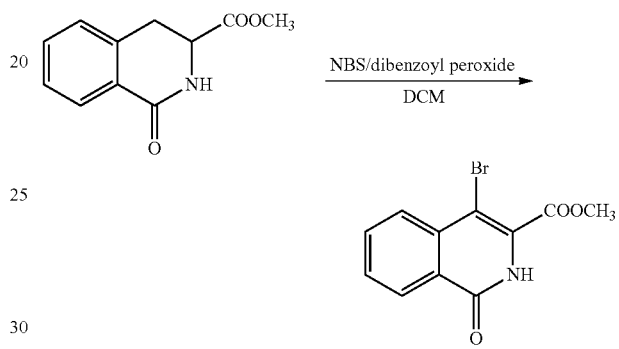

To a solution of compound 1-Oxo-1, 2, 3, 4-tetrahydroisoquinoline 3-carboxymethyl ester (3.56 g; 17.4 mmol) in 175 mL of methylene chloride was added N-bromosuccinimide (NBS) (6.26 g; 35.2 mmol) and benzyl peroxide (0.20 g; 0.8 mmol). The reaction was refluxed for 24 h. The reaction was cooled to room temperature and then washed with saturated NaHCO$_3$ (3×80 mL) and brine (80 mL). The organic layer was dried over anhydrous sodium sulfate. The drying agent was filtered and the filtrate was concentrated. The crude product was precipitated in 30 mL ethyl acetate and filtered, yielding the product (starting material 2) as a white solid (2.84 g; 57%), mp 186-187° C. $^1$H NMR (CDCl$_3$): 4.05 (s, 3H), 7.65-7.71 (t, 1H), 7.82-7.88 (t, 1H), 8.25-8.30 (d, 1H), 8.43-8.48 (d, 1H), 9.45 (s, 1H).

Synthesis of Compounds V-14 and V-15:

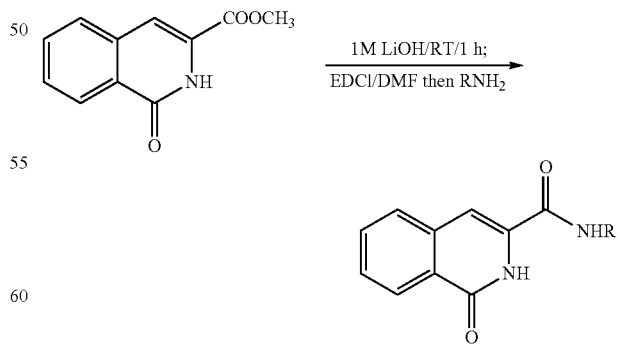

To a solution of starting material 1 (5 mmol) in 10 mL dioxane was added 1M lithium hydroxide (10 mL), and the reaction mixture was stirred at room temperature for 1 h. The solvent was removed on the rotary evaporator and the residue was treated with 20 mL water and acidified to pH 2, forming a precipitate. The precipitate was collected by suction filtration and washed with 20 mL ethyl acetate to give the corresponding acid as a white solid (80% yield), mp 230-232° C. $^1$H NMR (DMSO-D$_6$): 7.40 (s, 1H), 7.60-7.68 (t, 1H), 7.75-7.83 (t, 1H), 7.83-7.88 (d, 1H), 8.20-8.25 (d, 1 H), 11.80 (s, 1H). A solution of the acid (2 mmol) in dry N,N-dimethylformamide (DMF) (5 mL) was treated with 1-[3-(dimethylamino)propyl]-3-ethylcarbodiimide hydrochloride (EDCI) (0.38 g; 2 mmol), followed by 2 mmol of amine RNH$_2$ (R is D4 for Compound V-14; R is D5 for Compound V-15). The reaction mixture was stirred at room temperature overnight. The solvent was removed under vacuum and to the residue was added ethyl acetate (30 mL). The organic layer was washed with 5% aqueous HCl (3×10 mL), saturated aqueous NaHCO$_3$ (3×10 mL), and brine (10 mL). The organic layer was dried over anhydrous sodium sulfate. The drying agent was filtered and the solvent was removed. The crude product was purified by flash chromatography (silica gel/ethyl acetate/hexanes) to give the product.

Compound V-14: white solid (15% yield), mp 189-191° C. $^1$H NMR (CDCl$_3$) 4.68-4.73 (d, 2H), 7.20-8.08 (m, 10H), 10.88 (s, 1H).

Compound V-15: white solid (10% yield), mp 138-140° C. $^1$H NMR (DMSO-D$_6$) 4.48 (s, 2H), 6.34-6.36 (m, 1H), 6.60-6.62 (m, 1H), 7.35 (s, 1H), 7.57-7.80 (m, 4H), 8.20-8.24 (d, 1H).

Synthesis of Compounds V-1, V-2, V-3, V-4, and V-5:

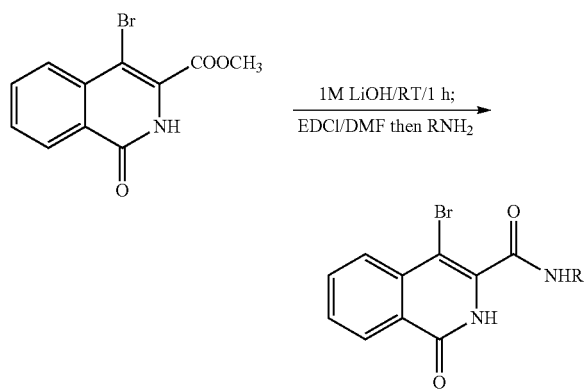

To a solution of starting material 2 (5 mmol) in 10 mL dioxane was added 1M lithium hydroxide (10 mL), and the reaction mixture was stirred at room temperature for 1 h. The solvent was removed on the rotary evaporator and the residue was treated with 20 mL water and acidified to pH 2, forming a precipitate. The precipitate was collected by suction filtration and washed with 20 mL ethyl acetate to give the corresponding acid as a white solid (64% yield). $^1$H NMR (DMSO-D$_6$): 7.65-7.73 (t, 1H), 7.84-8.00 (m, 2H), 8.20-8.30 (d, 1H), 11.80 (s, 1H). A solution of the acid (2 mmol) in dry N,N-dimethylformamide (DMF) (5 mL) was treated with 1-[3-(dimethylamino)propyl]-3-ethylcarbodiimide hydrochloride (EDCI) (0.38 g; 2 mmol), followed by 2 mmol of amine RNH$_2$ (R is D1 for Compound V-1; R is D2 for Compound V-2; R is D3 for Compound V-3; R is D4 for Compound V-4; R is D5 for Compound V-5). The reaction mixture was stirred at room temperature overnight. The solvent was removed under vacuum and the residue was added ethyl acetate (30 mL). The organic layer was washed with 5% aqueous HCl (3×10 mL), saturated aqueous NaHCO$_3$ (3×10 mL), and brine (10 mL). The organic layer was dried over anhydrous sodium sulfate. The drying agent was filtered and the solvent was removed. The crude product was purified by flash chromatography (silica gel/ethyl acetate/hexanes) to give the product.

Compound V-1: white solid (33% yield), mp 216-218° C. $^1$H NMR (DMSO-D$_6$) 6.78-8.42 (m, 13H), 10.50 (s, 1H), 11.72 (s, 1H).

Compound V-2: white solid (18% yield), mp 175-177° C. $^1$H NMR (CDCl$_3$) 2.95-3.00 (t, 2H), 3.82 (s, 3H), 3.80-3.86 (m, 2H), 6.80-6.89 (m, 3H), 7.23-7.30 (m, 1H), 7.60-7.67 (t, 1H), 7.67 (s, 1H), 7.76-7.83 (t, 1H), 8.02-8.05 (d, 1H), 8.43-8.46 (d, 1H), 9.78 (s, 1H).

Compound V-3: white solid (10% yield), mp 252-254° C. $^1$H NMR (DMSO-D$_6$) 3.05-3.15 (m, 4H), 3.70-3.80 (m, 4H), 6.92-7.00 (d, 2H), 7.52-7.60 (d, 2H), 7.60-7.68 (m, 1H), 7.84-7.96 (m, 2H), 8.23-8.28 (d, 1H), 10.82 (s, 1H), 12.17 (s, 1H).

Compound V-4: white solid (45% yield), mp 208-209° C. $^1$H NMR (DMSO-D$_6$) 4.45-4.52 (d, 2H), 7.23-8.27 (m, 9H), 9.28-9.37 (t, 1H), 12.10 (s, 1H).

Compound V-5: white solid (15% yield), mp 197-199° C. $^1$H NMR (CDCl$_3$) 4.68-4.73 (d, 2H), 6.37 (s, 2H), 7.41 (m, 1H), 7.60-7.68 (t, 1H), 7.74-7.82 (t, 1H), 8.00 (s, 1H), 8.02-8.08 (d, 1H), 8.40-8.46 (d, 1H), 9.90 (s, 1H).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus a combination of steps, elements, components, or constituents may be explicitly mentioned herein; however, all other combinations of steps, elements, components, and constituents are included, even though not explicitly stated.

What is claimed is:
1. A compound of the following formula:

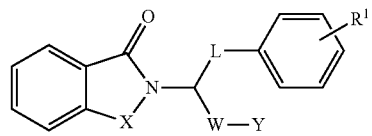

or a pharmaceutically acceptable salt thereof, wherein:
L is substituted or substituted C$_{1-8}$ alkyl, substituted or unsubstituted C$_{2-8}$ alkenyl, substituted or unsubstituted C$_{2-8}$ alkyl, substituted or unsubstituted C$_{1-8}$ heteroalkyl, substituted or unsubstituted C$_{2-8}$ heteroalkenyl, or substituted or unsubstituted C$_{2-8}$heteroalkynyl;

R$^1$ is hydrogen, substituted or unsubstituted C$_{1-12}$ alkenyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl;

W is C(O)NR³—NR⁴C(O) or

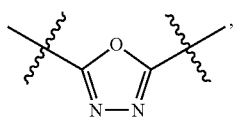

wherein R³ and R⁴ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heterocycloalkyl, substituted or unsubstituted cycloalkylalkyl, or substituted or unsubstituted heterocycloalkylalkyl;

X is $CH_2$ or S; and

Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

2. The compound of claim 1, wherein the compound has the following formula:

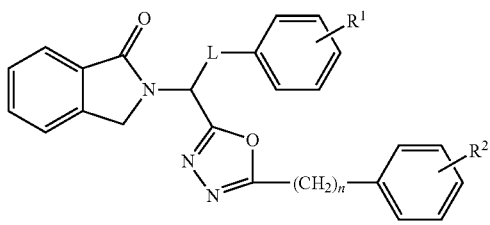

or a pharmaceutically acceptable salt thereof, wherein;

n is 0 to 5;

L is substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{1-8}$ heteroalkyl, substituted or unsubstituted $C_{2-8}$ heteroalkenyl, or substituted or unsubstituted $C_{2-8}$ heteroalkynyl; and R¹ and R² are each independently selected from hydrogen, halogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

3. The compound of claim 2, wherein the compound has the following formula:

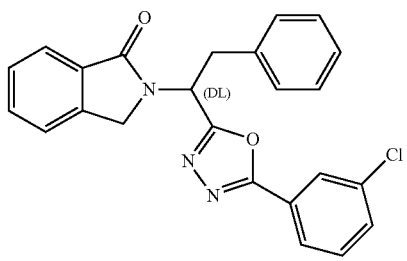 [SMILES: O=C1c2ccccc2CN1C(Cc1ccccc1)c1nnc(-c2cccc(Cl)c2)o1]

or a pharmaceutically acceptable salt thereof.

4. The compound of claim 1, wherein the compound has the following formula:

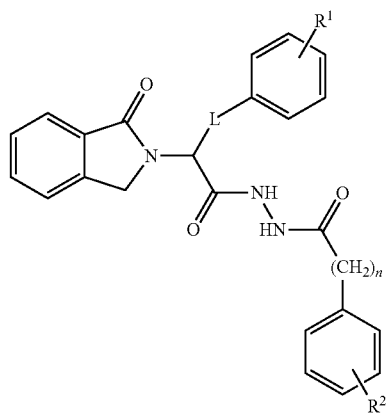

or a pharmaceutically acceptable salt thereof, wherein:

n is 0 to 5;

L is substituted or unsubstituted $C_{1-8}$ alkyl, substituted or unsubstituted $C_{2-8}$ alkenyl, substituted or unsubstituted $C_{2-8}$ alkynyl, substituted or unsubstituted heteroalkyl, substituted or unsubstituted heteroalkenyl, or substituted or unsubstituted heteroalkynyl; and R¹ and R² are each independently selected from hydrogen, halogen, substituted or unsubstituted $C_{1-12}$ alkyl, substituted or unsubstituted $C_{1-12}$ haloalkyl, substituted or unsubstituted $C_{2-12}$, alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

5. A composition comprising the compound of claim 1 and a pharmaceutically acceptable carrier.

6. A method of treating a viral infection in a subject comprising administering to the subject a therapeutically effective amount of a compound of the following formula:

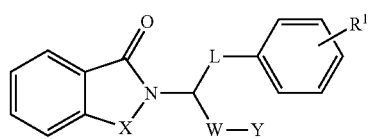

or a pharmaceutically acceptable salt or prodrug thereof wherein:

L is substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{1-8}$ heteroalkyl, substituted, or unsubstituted $C_{2-8}$ heteroalkenyl, or substituted or unsubstituted $C_{2-8}$ heteroalkynyl;

$R^1$ is hydrogen, substituted or unsubstituted $C_{1-2}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkytalkyl;

W is $C(O)NR^3$—$NR^4C(O)$ or

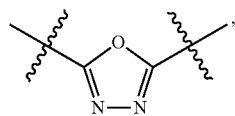

wherein $R^3$ and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl;

X is $CH_2$ or S; and

Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

7. The method claim 6, wherein the viral infection is Hepatitis C Virus.

8. The method claim 6, wherein the viral infection is a *Flavivirus* infection.

9. The method of claim 8, wherein the *Flavivirus* is Dengue Virus serotype DEN-1, Dengue Virus serotype DEN-2, Dengue Virus serotype DEN-3, or Dengue Virus serotype DEN-4, West Nile Virus (WNV), or Japanese Encephalitis Virus.

* * * * *